(12) United States Patent
Stransky et al.

(10) Patent No.: US 11,261,497 B2
(45) Date of Patent: Mar. 1, 2022

(54) PRKC FUSIONS

(71) Applicant: BLUEPRINT MEDICINES CORPORATION, Cambridge, MA (US)

(72) Inventors: Nicolas Stransky, Charlestown, MA (US); Joseph L. Kim, Wayland, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 16/513,176

(22) Filed: Jul. 16, 2019

(65) Prior Publication Data

US 2020/0181715 A1    Jun. 11, 2020

Related U.S. Application Data

(62) Division of application No. 15/326,359, filed as application No. PCT/US2015/040560 on Jul. 15, 2015, now Pat. No. 10,370,724.

(60) Provisional application No. 62/025,865, filed on Jul. 17, 2014.

(51) Int. Cl.

| | |
|---|---|
| C12Q 1/68 | (2018.01) |
| C07H 21/04 | (2006.01) |
| C12Q 1/6886 | (2018.01) |
| C07K 16/30 | (2006.01) |
| C12N 15/113 | (2010.01) |
| G01N 33/574 | (2006.01) |

(52) U.S. Cl.
CPC ............ *C12Q 1/6886* (2013.01); *C07K 16/30* (2013.01); *C12N 15/1138* (2013.01); *G01N 33/57423* (2013.01); *C12Q 2600/156* (2013.01)

(58) Field of Classification Search
None
See application file for complete search history.

(56) References Cited

U.S. PATENT DOCUMENTS

2012/0171219 A1    7/2012  Acevedo-Duncan et al.

FOREIGN PATENT DOCUMENTS

| WO | WO 2013/113942 A2 | 8/2013 |
|---|---|---|
| WO | WO 2014/038887 A1 | 3/2014 |

OTHER PUBLICATIONS

International Patent Application No. PCT/US2015/040560, filed Jul. 15, 2015, by Blueprint Medicines Corp.: International Search Report and Written Opinion, dated Nov. 17, 2015.

Bridge, J.A. et al. (2013) "Identification of a novel, recurrent SLC44A1-PRKCA fusion in papillary glioneuronal tumor" *Brain Pathology*, 23(2):121-128.

GenBank Accession No. NM_006547, "*Homo sapiens* insulin like growth factor 2 mRNA binding protein 3 (IGF2BP3), mRNA" PRI May 6, 2017, 6 pages.

GenBank Accession No. NM_002737, "*Homo sapiens* protein kinase C alpha (PRKCA), mRNA" PRI May 28, 2017, 9 pages.

(Continued)

*Primary Examiner* — Jeanine A Goldberg
(74) *Attorney, Agent, or Firm* — Finnegan, Henderson, Farabow, Garrett & Dunner, LLP

(57) ABSTRACT

The invention provides PRKC gene fusions, PRKC fusion proteins, and fragments of those genes and polypeptides. The invention further provides methods of diagnosing and treating diseases or disorders associated with PRKC fusions, such as conditions mediated by aberrant PRKC expression or activity, or overexpression of PRKC.

7 Claims, 9 Drawing Sheets

Specification includes a Sequence Listing.

(56) References Cited

OTHER PUBLICATIONS

GenBank Accession No. NM_025185, "*Homo sapiens* tetratricopeptide repeat, ankyrin repeat and coiled-coil containing 2 (TANC2), mRNA" PRI Apr. 22, 2017, 11 pages.
GenBank Accession No. NM_001116, "*Homo sapiens* adenylate cyclase 9 (ADCY9), mRNA" PRI May 27, 2017, 9 pages.
GenBank Accession No. NM_002738, "*Homo sapiens* protein kinase C beta (PRKCB), transcript variant 2, mRNA" PRI Jun. 14, 2017, 8 pages.
GenBank Accession No. NM_001142451, "*Homo sapiens* sphingolipid transporter 1 (putative) (SPNS1), transcript variant 4, mRNA" PRI May 30, 2016, 4 pages.
Plaszczyca, A. et al. (2014) "Fusions involving protein kinase C and membrane-associated proteins in benign fibrous histiocytoma" *Intl J Biochem Cell Biol,* 53:475-481.
Soda, M. et al. (2007) "Identification of the transforming EML4-ALK fusion gene in non-small-cell lung cancer" *Nature,* 448:561-566.
Stephens, P.J. et al. (2009) "Complex landscapes of somatic rearrangement in human breast cancer genomes" *Nature,* 462:1005-1010, with Supplementary Information, 2 pages.
Stransky, N. et al. (2014) "The landscape of kinase fusions in cancer" *Nature Commun,* 5:4846, DOI: 10.1038/ncommms5846, 10 pages.

FIG. 1

```
ATGAACAAAC TGTATATCGG AAACCTCAGC GAGAACGCCG CCCCCTCGGA CCTAGAAAGT    60
ATCTTCAAGG ACGCCAAGAT CCCGGTGTCG GGACCCTTCC TGGTGAAGAC TGGCTACGCG   120
TTCGTGGACT GCCCGGACGA GAGCTGGGCC CTCAAGGCCA TCGAGGCGCT TTCAGGTAAA   180
ATAGAACTGC ACGGGAAACC CATAGAAGTT GAGCACTCGG TCCCAAAAAG GCAAAGGATT   240
CGGAAACTTC AGATACGAAA TATCCCGCCT CATTTACAGT GGGAGGTGCT GGATAGTTTA   300
CTAGTCCAGT ATGGAGTGGT GGAGAGCTGT GAGCAAGTGA ACACTGACTC GGAAACTGCA   360
GTTGTAAATG TAACCTATTC CAGTAAGGAC CAAGCTAGAC AAGCACTAGA CAAACTGAAT   420
GGATTTCAGT TAGAGAATTT CACCTTGAAA GTAGCCTATA TCCCTGATGA AATGGCCGCC   480
CAGCAAAACC CCTTGCAGCA GCCCCGAGGT CGCCGGGGGC TTGGGCAGAG GGGCTCCTCA   540
AGGCAGGGGT CTCCAGGATC CGTATCCAAG CAGAAACCAT GTGATTTGCC TCTGCGCCTG   600
CTGGTTCCCA CCCAATTTGT TGGAGCCATC ATAGGAAAAG AAGGTGCCAC CATTCGGAAC   660
ATCACCAAAC AGACCCAGTC TAAAATCGAT GTCCACCGTA AGAAAATGC GGGGGCTGCT   720
GAGAAGTCGA TTACTATCCT CTCTACTCCT GAAGGCACCT CTGCGGCTTG TAAGTCTATT   780
CTGGAGATTA TGCATAAGGA AGCTCAAGAT ATAAAATTCA CAGAAGAGAT CCCCTTGAAG   840
ATTTTAGCTC ATAATAACTT TGTTGGACGT CTTATTGGTA AGAAGGAAG AAATCTTAAA   900
AAAATTGAGC AAGACACAGA CACTAAAATC ACGATATCTC CATTGCAGGA ATTGACGCTG   960
TATAATCCAG AACGCACTAT TACAGTTAAA GGCAATGTTG AGACATGTGC CAAAGCTGAG  1020
GAGGAGATCA TGAAGAAAAT CAGGGAGTCT TATGAAAATG ATATTGCTTC TATGAATCTT  1080
CAAGCACATT TAATTCCTGG ATTAAATCTG AACGCCTTGG GTCTGTTCCC ACCCACTTCA  1140
GGGATGCCAC CTCCCACCTC AGGGCCCCCT TCAGCCATGA CTCCTCCCTA CCCGCAGTTT  1200
GAG/GACCCCA GGAGCAAGCA CAAGTTCAAA ATCCACACTT ACGGAAGCCC CACCTTCTGC  1260
GATCACTGTG GGTCACTGCT CTATGGACTT ATCCATCAAG GGATGAAATG TGACACCTGC  1320
GATATGAACG TTCACAAGCA ATGCGTCATC AATGTCCCCA GCCTCTGCGG AATGGATCAC  1380
ACTGAGAAGA GGGGGCGGAT TTACCTAAAG GCTGAGGTTG CTGATGAAAA GCTCCATGTC  1440
ACAGTACGAG ATGCAAAAAA TCTAATCCCT ATGGATCCAA ACGGGCTTTC AGATCCTTAT  1500
GTGAAGCTGA AACTTATTCC TGATCCCAAG AATGAAAGCA AGCAAAAAAC CAAAACCATC  1560
CGCTCCACAC TAAATCCGCA GTGGAATGAG TCCTTTACAT TCAAATTGAA ACCTTCAGAC  1620
AAAGACCGAC GACTGTCTGT AGAAATCTGG GACTGGGATC GAACAACAAG GAATGACTTC  1680
ATGGGATCCC TTTCCTTTGG AGTTTCGGAG CTGATGAAGA TGCCGGCCAG TGGATGGTAC  1740
AAGTTGCTTA ACCAAGAAGA AGGTGAGTAC TACAACGTAC CCATTCCGGA AGGGGACGAG  1800
GAAGGAAACA TGGAACTCAG GCAGAAATTC GAGAAAGCCA AACTTGGCCC TGCTGGCAAC  1860
AAAGTCATCA GTCCCTCTGA AGACAGGAAA CAACCTTCCA ACAACCTTGA CCGAGTGAAA  1920
CTCACGGACT TCAATTTCCT CATGGTGTTG GGAAAGGGGA GTTTTGGAAA GGTGATGCTT  1980
GCCGACAGGA AGGGCACAGA AGAACTGTAT GCAATCAAAA TCCTGAAGAA GGATGTGGTG  2040
ATTCAGGATG ATGACGTGGA GTGCACCATG GTAGAAAAGC GAGTCTTGGC CCTGCTTGAC  2100
AAACCCCCGT TCTTGACGCA GCTGCACTCC TGCTTCCAGA CAGTGGATCG GCTGTACTTC  2160
GTCATGGAAT ATGTCAACGG TGGGGACCTC ATGTACCACA TTCAGCAAGT AGGAAAATTT  2220
AAGGAACCAC AAGCAGTATT CTATGCGGCA GAGATTTCCA TCGGATTGTT CTTTCTTCAT  2280
AAAAGAGGAA TCATTTATAG GGATCTGAAG TTAGATAACG TCATGTTGGA TTCAGAAGGA  2340
CATATCAAAA TTGCTGACTT TGGGATGTGC AAGGAACACA TGATGGATGG AGTCACGACC  2400
AGGACCTTCT GTGGGACTCC AGATTATATC GCCCCAGAGA TAATCGCTTA TCAGCCGTAT  2460
GGAAAATCTG TGGACTGGTG GGCCTATGGC GTCCTGTTGT ATGAAATGCT TGCCGGGCAG  2520
CCTCCATTTG ATGGTGAAGA TGAAGACGAG CTATTTCAGT CTATCATGGA GCACAACGTT  2580
TCCTATCCAA AATCCTTGTC CAAGGAGGCT GTTTCTATCT GCAAAGGACT GATGACCAAA  2640
CACCCAGCCA AGCGGCTGGG CTGTGGGCCT GAGGGGGAGA GGGACGTGAG AGAGCATGCC  2700
TTCTTCCGGA GGATCGACTG GGAAAAACTG GAGAACAGGG AGATCCAGCC ACCATTCAAG  2760
CCCAAAGTGT GTGGCAAAGG AGCAGAGAAC TTTGACAAGT TCTTCACACG AGGACAGCCC  2820
GTCTTAACAC CACCTGATCA GCTGGTTATT GCTAACATAG ACCAGTCTGA TTTTGAAGGG  2880
TTCTCGTATG TCAACCCCCA GTTTGTGCAC CCATCTTAC AGAGTGCAGT ATGA          2934
```

(SEQ ID NO:1)

FIG. 2

```
MNKLYIGNLS ENAAPSDLES IFKDAKIPVS GPFLVKTGYA FVDCPDESWA LKAIEALSGK  60
IELHGKPIEV EHSVPKRQRI RKLQIRNIPP HLQWEVLDSL LVQYGVVESC EQVNTDSETA 120
VVNVTYSSKD QARQALDKLN GFQLENFTLK VAYIPDEMAA QQNPLQQPRG RRGLGQRGSS 180
RQGSPGSVSK QKPCDLPLRL LVPTQFVGAI IGKEGATIRN ITKQTQSKID VHRKENAGAA 240
EKSITILSTP EGTSAACKSI LEIMHKEAQD IKFTEEIPLK ILAHNNFVGR LIGKEGRNLK 300
KIEQDTDTKI TISPLQELTL YNPERTITVK GNVETCAKAE EEIMKKIRES YENDIASMNL 360
QAHLIPGLNL NALGLFPPTS GMPPPTSGPP SAMTPPYPQF E/DPRSKHKFK IHTYGSPTFC 420
DHCGSLLYGL IHQGMKCDTC DMNVHKQCVI NVPSLCGMDH TEKRGRIYLK AEVADEKLHV 480
TVRDAKNLIP MDPNGLSDPY VKLKLIPDPK NESKQKTKTI RSTLNPQWNE SFTFKLKPSD 540
KDRRLSVEIW DWDRTTRNDF MGSLSFGVSE LMKMPASGWY KLLNQEEGEY YNVPIPEGDE 600
EGNMELRQKF EKAKLGPAGN KVISPSEDRK QPSNNLDRVK LTDFNFLMVL GKGSFGKVML 660
ADRKGTEELY AIKILKKDVV IQDDDVECTM VEKRVLALLD KPPFLTQLHS CFQTVDRLYF 720
VMEYVNGGDL MYHIQQVGKF KEPQAVFYAA EISIGLFFLH KRGIIYRDLK LDNVMLDSEG 780
HIKIADFGMC KEHMMDGVTT RTFCGTPDYI APEIIAYQPY GKSVDWWAYG VLLYEMLAGQ 840
PPFDGEDEDE LFQSIMEHNV SYPKSLSKEA VSICKGLMTK HPAKRLGCGP EGERDVREHA 900
FFRRIDWEKL ENREIQPPFK PKVCGKGAEN FDKFFTRGQP VLTPPDQLVI ANIDQSDFEG 960
FSYVNPQFVH PILQSAV                                                977

(SEQ ID NO:2)
```

FIG. 3

```
ATGTTTCGGA ATAGTCTCAA GATGCTGCTT ACTGGTGGGA AATCAAGTCG TAAAAACAGG    60
TCAAGTGATG GAGGGAGCGA GGAACCACCG GATCGAAGAC AGTCAAGTGT AGACTCTCGC   120
CAAAGCCGCT CTGGGCAAG/T ACGAGATGCA AAAAATCTAA TCCCTATGGA TCCAAACGGG   180
CTTTCAGATC CTTATGTGAA GCTGAAACTT ATTCCTGATC CCAAGAATGA AAGCAAGCAA   240
AAAACCAAAA CCATCCGCTC CACACTAAAT CCGCAGTGGA ATGAGTCCTT TACATTCAAA   300
TTGAAACCTT CAGACAAAGA CCGACGACTG TCTGTAGAAA TCTGGGACTG GGATCGAACA   360
ACAAGGAATG ACTTCATGGG ATCCCTTTCC TTTGGAGTTT CGGAGCTGAT GAAGATGCCG   420
GCCAGTGGAT GGTACAAGTT GCTTAACCAA GAAGAAGGTG AGTACTACAA CGTACCCATT   480
CCGGAAGGGG ACGAGGAAGG AAACATGGAA CTCAGGCAGA AATTCGAGAA AGCCAAACTT   540
GGCCCTGCTG GCAACAAAGT CATCAGTCCC TCTGAAGACA GGAAACAACC TTCCAACAAC   600
CTTGACCGAG TGAAACTCAC GGACTTCAAT TTCCTCATGG TGTTGGGAAA GGGGAGTTTT   660
GGAAAGGTGA TGCTTGCCGA CAGGAAGGGC ACAGAAGAAC TGTATGCAAT CAAAATCCTG   720
AAGAAGGATG TGGTGATTCA GGATGATGAC GTGGAGTGCA CCATGGTAGA AAAGCGAGTC   780
TTGGCCCTGC TTGACAAACC CCCGTTCTTG ACGCAGCTGC ACTCCTGCTT CCAGACAGTG   840
GATCGGCTGT ACTTCGTCAT GGAATATGTC AACGGTGGGG ACCTCATGTA CCACATTCAG   900
CAAGTAGGAA AATTTAAGGA ACCACAAGCA GTATTCTATG CGGCAGAGAT TTCCATCGGA   960
TTGTTCTTTC TTCATAAAAG AGGAATCATT TATAGGGATC TGAAGTTAGA TAACGTCATG  1020
TTGGATTCAG AAGGACATAT CAAAATTGCT GACTTTGGGA TGTGCAAGGA ACACATGATG  1080
GATGGAGTCA CGACCAGGAC CTTCTGTGGG ACTCCAGATT ATATCGCCCC AGAGATAATC  1140
GCTTATCAGC CGTATGGAAA ATCTGTGGAC TGGTGGGCCT ATGGCGTCCT GTTGTATGAA  1200
ATGCTTGCCG GGCAGCCTCC ATTTGATGGT GAAGATGAAG ACGAGCTATT TCAGTCTATC  1260
ATGGAGCACA ACGTTCCTA TCCAAAATCC TTGTCCAAGG AGGCTGTTTC TATCTGCAAA  1320
GGACTGATGA CCAAACACCC AGCCAAGCGG CTGGGCTGTG GCCTGAGGG GGAGAGGGAC  1380
GTGAGAGAGC ATGCCTTCTT CCGGAGGATC GACTGGAAA AACTGGAGAA CAGGGAGATC  1440
CAGCCACCAT TCAAGCCCAA AGTGTGTGGC AAAGGAGCAG AGAACTTTGA CAAGTTCTTC  1500
ACACGAGGAC AGCCCGTCTT AACACCACCT GATCAGCTGG TTATTGCTAA CATAGACCAG  1560
TCTGATTTTG AAGGGTTCTC GTATGTCAAC CCCCAGTTTG TGCACCCCAT CTTACAGAGT  1620
GCAGTATGA                                                         1629
```

(SEQ ID NO:3)

FIG. 4

```
MFRNSLKMLL TGGKSSRKNR SSDGGSEEPP DRRQSSVDSR QSRSGQVRDA KNLIPMDPNG  60
LSDPYVKLKL IPDPKNESKQ KTKTIRSTLN PQWNESFTFK LKPSDKDRRL SVEIWDWDRT 120
TRNDFMGSLS FGVSELMKMP ASGWYKLLNQ EEGEYYNVPI PEGDEEGNME LRQKFEKAKL 180
GPAGNKVISP SEDRKQPSNN LDRVKLTDFN FLMVLGKGSF GKVMLADRKG TEELYAIKIL 240
KKDVVIQDDD VECTMVEKRV LALLDKPPFL TQLHSCFQTV DRLYFVMEYV NGGDLMYHIQ 300
QVGKFKEPQA VFYAAEISIG LFFLHKRGII YRDLKLDNVM LDSEGHIKIA DFGMCKEHMM 360
DGVTTRTFCG TPDYIAPEII AYQPYGKSVD WWAYGVLLYE MLAGQPPFDG EDEDELFQSI 420
MEHNVSYPKS LSKEAVSICK GLMTKHPAKR LGCGPEGERD VREHAFFRRI DWEKLENREI 480
QPPFKPKVCG KGAENFDKFF TRGQPVLTPP DQLVIANIDQ SDFEGFSYVN PQFVHPILQS 540
AV                                                              542
```

(SEQ ID NO:4)

FIG. 5A

```
ATGGCTTCCC CACCCCACCA GCAGCTGCTG CATCACCACA GCACCGAGGT GAGCTGCGAC   60
TCCAGCGGGG ACAGCAACAG CGTGCGCGTC AAGATCAACC CCAAGCAGCT GTCCTCCAAC  120
AGCCACCCCA AGCACTGCAA ATACAGCATC TCCTCTAGCT GCAGCAGCTC TGGGGACTCC  180
GGGGGCGTCC CCCGGCGAGT GGGCGGCGGA GGCCGGCTGC GCAGGCAGAA GAAGCTGCCC  240
CAGCTGTTCG AGAGGGCCTC CAGCCGCTGG TGGGACCCCA AGTTCGACTC GGTGAACCTG  300
GAGGAGGCCT GCCTGGAGCG CTGCTTCCCG CAGACCCAGC GCCGGTTCCG GTATGCGCTC  360
TTCTACATCG GCTTCGCCTG CCTTCTGTGG AGCATCTATT TTGCGGTCCA CATGAGATCC  420
AGACTGATCG TCATGGTCGC CCCCGCGCTG TGCTTCCTCC TGGTGTGTGT GGGCTTCTTT  480
CTGTTTACCT TCACCAAGCT GTACGCCCGG CATTACGCGT GGACCTCGCT GGCTCTCACC  540
CTGCTGGTGT TCGCCCTGAC CCTGGCTGCG CAGTTCCAGG TCTTGACGCC TGTCTCAGGA  600
CGCGGCGACA GCTCCAACCT TACGGCCACA GCCCGGCCCA CAGATACTTG CTTATCTCAA  660
GTGGGGAGCT TCTCCATGTG CATCGAAGTG CTCTTTTTGC TCTATACCGT CATGCACTTA  720
CCTTTGTACC TGAGTTTGTG TCTGGGGGTG GCCTACTCTG TCCTTTTCGA GACCTTTGGC  780
TACCATTTCC GGGATGAAGC CTGCTTCCCC TCGCCCGGAG CCGGGGCCCT GCACTGGGAG  840
CTGCTGAGCA GGGGGCTGCT CCACGGCTGC ATCCACGCCA TCGGGTCCA  CCTGTTCGTC  900
ATGTCCCAGG TGAGGTCCAG GAGCACCTTC CTCAAGGTGG GGCAATCCAT TATGCACGGG  960
AAGGACCTGG AAGTGGAAAA AGCCCTCAAA GAGAGGATGA TTCATTCCGT GATGCCAAGA 1020
ATCATAGCCG ATGACTTAAT GAAGCAGGGA GATGAGGAGA GTGAGAATTC TGTCAAGAGG 1080
CATGCCACCT CGAGCCCCAA GAACAGGAAG AAAAAGTCTT CCATCCAAAA AGCTCCTATA 1140
GCCTTCCGCC CTTTTAAGAT GCAGCAGATC GAAGAAGTCA GTATTTATT  TGCAGATATC 1200
GTGGGCTTCA CCAAGATGAG TGCCAACAAG TCTGCCCACG CCCTGGTGGG TCTCCTGAAC 1260
GATCTGTTCG GTCGCTTCGA CCGCCTGTGT GAGGAGACCA AGTGTGAGAA AATCAGCACC 1320
CTGGGAGACT GTTACTACTG CGTGGCGGGC TGTCCCGAGC CCGGGCCGA  CCATGCCTAC 1380
TGCTGCATCG AGATGGGCCT GGGCATGATC AAGGCCATCG AGCAGTTCTG CCAGGAGAAG 1440
AAGGAGATGG TGAACATGAG AGTCGGGGTG CACACGGGCA CCGTCCTTTG CGGCATCCTG 1500
GGCATGAGGA GGTTTAAATT TGACGTGTGG TCCAACGATG TGAACCTGGC CAATCTCATG 1560
GAGCAGCTGG GAGTGGCCGG CAAAGTTCAC ATTTCTGAGG CCACCGCAAA ATACTTAGAT 1620
GACCGGTACG AAATGGAAGA TGGGAAAGTT ATTGAACGGC TGGGCCAGAG CGTGGTTGCT 1680
GACCAGTTGA AAG/TTTGCTG CTTTGTGGTG CACAAGCGGT GCCATGAATT TGTCACATTC 1740
TCCTGCCCTG GCGCTGACAA GGGTCCAGCC TCCGATGACC CCGCAGCAA  ACACAAGTTT 1800
AAGATCCACA CGTACTCCAG CCCCACGTTT TGTGACCACT GTGGGTCACT GCTGTATGGA 1860
CTCATCCACC AGGGGATGAA ATGTGACACC TGCATGATGA ATGTGCACAA GCGCTGCGTG 1920
ATGAATGTTC CCAGCCTGTG TGGCACGGAC CACACGGAGC GCCGCGGCCG CATCTACATC 1980
CAGGCCCACA TCGACAGGGA CGTCCTCATT GTCCTCGTAA GAGATGCTAA AAACCTTGTA 2040
CCTATGGACC CCAATGGCCT GTCAGATCCC TACGTAAAAC TGAAACTGAT TCCCGATCCC 2100
AAAAGTGAGA GCAAACAGAA GACCAAAACC ATCAAATGCT CCCTCAACCC TGAGTGGAAT 2160
GAGACATTTA GATTTCAGCT GAAAGAATCG GACAAAGACA GAAGACTGTC AGTAGAGATT 2220
TGGGATTGGG ATTTGACCAG CAGGAATGAC TTCATGGGAT CTTTGTCCTT TGGGATTTCT 2280
GAACTTCAGA AAGCCAGTGT TGATGGCTGG TTTAAGTTAC TGAGCCAGGA GGAAGGCGAG 2340
TACTTCAATG TGCCTGTGCC ACCAGAAGGA AGTGAGGCCA ATGAAGAACT GCGGCAGAAA 2400
TTTGAGAGGG CCAAGATCAG TCAGGGAACC AAGGTCCCGG AAGAAAAGAC GACCAACACT 2460
GTCTCCAAAT TTGACAACAA TGGCAACAGA GACCGGATGA AACTGACCGA TTTTAACTTC 2520
CTAATGGTGC TGGGGAAAGG CAGCTTTGGC AAGGTCATGC TTTCAGAACG AAAAGGCACA 2580
GATGAGCTCT ATGCTGTGAA GATCCTGAAG AAGGACGTTG TGATCCAAGA TGATGACGTG 2640
GAGTGCACTA TGGTGGAGAA GCGGGTGTTG GCCCTGCCTG GAAGCCGCC  CTTCCTGACC 2700
CAGCTCCACT CCTGCTTCCA GACCATGGAC CGCCTGTACT TTGTGATGGA GTACGTGAAT 2760
GGGGGCGACC TCATGTATCA CATCCAGCAA GTCGGCCGGT TCAAGGAGCC CCATGCTGTA 2820
TTTTACGCTG CAGAAATTGC CATCGGTCTG TTCTTCTTAC AGAGTAAGGG CATCATTTAC 2880
CGTGACCTAA AACTTGACAA CGTGATGCTC GATTCTGAGG ACACATCAA  GATTGCCGAT 2940
TTTGGCATGT GTAAGGAAAA CATCTGGGAT GGGGTGACAA CCAAGACATT CTGTGGCACT 3000
CCAGACTACA TCGCCCCCGA GATAATTGCT TATCAGCCCT ATGGGAAGTC CGTGGATTGG 3060
```

FIG. 5B

```
TGGGCATTTG GAGTCCTGCT GTATGAAATG TTGGCTGGGC AGGCACCCTT TGAAGGGGAG    3120
GATGAAGATG AACTCTTCCA ATCCATCATG GAACACAACG TAGCCTATCC CAAGTCTATG    3180
TCCAAGGAAG CTGTGGCCAT CTGCAAAGGG CTGATGACCA AACACCCAGG CAAACGTCTG    3240
GGTTGTGGAC CTGAAGGCGA ACGTGATATC AAAGAGCATG CATTTTTCCG GTATATTGAT    3300
TGGGAGAAAC TTGAACGCAA AGAGATCCAG CCCCCTTATA AGCCAAAAGC TTGTGGGCGA    3360
AATGCTGAAA ACTTCGACCG ATTTTTCACC CGCCATCCAC CAGTCCTAAC ACCTCCCGAC    3420
CAGGAAGTCA TCAGGAATAT TGACCAATCA GAATTCGAAG GATTTTCCTT TGTTAACTCT    3480
GAATTTTTAA AACCCGAAGT CAAGAGCTAA                                     3510
```

(SEQ ID NO:5)

FIG. 6

```
MASPPHQQLL HHHSTEVSCD SSGDSNSVRV KINPKQLSSN SHPKHCKYSI SSSCSSSGDS   60
GGVPRRVGGG GRLRRQKKLP QLFERASSRW WDPKFDSVNL EEACLERCFP QTQRRFRYAL  120
FYIGFACLLW SIYFAVHMRS RLIVMVAPAL CFLLVCVGFF LFTFTKLYAR HYAWTSLALT  180
LLVFALTLAA QFQVLTPVSG RGDSSNLTAT ARPTDTCLSQ VGSFSMCIEV LFLLYTVMHL  240
PLYLSLCLGV AYSVLFETFG YHFRDEACFP SPGAGALHWE LLSRGLLHGC IHAIGVHLFV  300
MSQVRSRSTF LKVGQSIMHG KDLEVEKALK ERMIHSVMPR IIADDLMKQG DEESENSVKR  360
HATSSPKNRK KKSSIQKAPI AFRPFKMQQI EEVSILFADI VGFTKMSANK SAHALVGLLN  420
DLFGRFDRLC EETKCEKIST LGDCYYCVAG CPEPRADHAY CCIEMGLGMI KAIEQFCQEK  480
KEMVNMRVGV HTGTVLCGIL GMRRFKFDVW SNDVNLANLM EQLGVAGKVH ISEATAKYLD  540
DRYEMEDGKV IERLGQSVVA DQLKVCCFVV HKRCHEFVTF SCPGADKGPA SDDPRSKHKF  600
KIHTYSSPTF CDHCGSLLYG LIHQGMKCDT CMMNVHKRCV MNVPSLCGTD HTERRGRIYI  660
QAHIDRDVLI VLVRDAKNLV PMDPNGLSDP YVKLKLIPDP KSESKQKTKT IKCSLNPEWN  720
ETFRFQLKES DKDRRLSVEI WDWDLTSRND FMGSLSFGIS ELQKASVDGW FKLLSQEEGE  780
YFNVPVPPEG SEANEELRQK FERAKISQGT KVPEEKTTNT VSKFDNNGNR DRMKLTDFNF  840
LMVLGKGSFG KVMLSERKGT DELYAVKILK KDVVIQDDDV ECTMVEKRVL ALPGKPPFLT  900
QLHSCFQTMD RLYFVMEYVN GGDLMYHIQQ VGRFKEPHAV FYAAEIAIGL FFLQSKGIIY  960
RDLKLDNVML DSEGHIKIAD FGMCKENIWD GVTTKTFCGT PDYIAPEIIA YQPYGKSVDW 1020
WAFGVLLYEM LAGQAPFEGE DEDELFQSIM EHNVAYPKSM SKEAVAICKG LMTKHPGKRL 1080
GCGPEGERDI KEHAFFRYID WEKLERKEIQ PPYKPKACGR NAENFDRFFT RHPPVLTPPD 1140
QEVIRNIDQS EFEGFSFVNS EFLKPEVKS                                  1169

(SEQ ID NO:6)
```

FIG. 7

```
ATGGCCGGGT CCGACACCGC GCCCTTCCTC AGCCAGGCGG ATGACCCGGA CGACGGGCCA   60
GTGCCTGGCA CCCCGGGGTT GCCAGGGTCC ACGGGGAACC CGAAGTCCGA GGAGCCCGAG  120
GTCCCGGACC AGGAGGGGCT GCAGCGCATC ACCGGCCTGT CTCCCGGCCG TTCGGCTCTC  180
ATAGTGGCGG TGCTGTGCTA CATCAATCTC CTGAACTACA TGGACCGCTT CACCGTGGCT  240
GGCGTCCTTC CCGACATCGA GCAGTTCTTC AACATCGGGG ACAGTAGCTC TGGGCTCATC  300
CAGACCG/TTT GCTGCTTTGT GGTGCACAAG CGGTGCCATG AATTTGTCAC ATTCTCCTGC  360
CCTGGCGCTG ACAAGGGTCC AGCCTCCGAT GACCCCCGCA GCAAACACAA GTTTAAGATC  420
CACACGTACT CCAGCCCCAC GTTTTGTGAC CACTGTGGGT CACTGCTGTA TGGACTCATC  480
CACCAGGGGA TGAAATGTGA CACCTGCATG ATGAATGTGC ACAAGCGCTG CGTGATGAAT  540
GTTCCCAGCC TGTGTGGCAC GGACCACACG GAGCGCCGCG GCCGCATCTA CATCCAGGCC  600
CACATCGACA GGGACGTCCT CATTGTCCTC GTAAGAGATG CTAAAAACCT TGTACCTATG  660
GACCCCAATG GCCTGTCAGA TCCCTACGTA AAACTGAAAC TGATTCCCGA TCCCAAAAGT  720
GAGAGCAAAC AGAAGACCAA AACCATCAAA TGCTCCCTCA ACCCTGAGTG GAATGAGACA  780
TTTAGATTTC AGCTGAAAGA ATCGGACAAA GACAGAAGAC TGTCAGTAGA GATTTGGGAT  840
TGGGATTTGA CCAGCAGGAA TGACTTCATG GGATCTTTGT CCTTTGGGAT TTCTGAACTT  900
CAGAAAGCCA GTGTTGATGG CTGGTTTAAG TTACTGAGCC AGGAGGAAGG CGAGTACTTC  960
AATGTGCCTG TGCCACCAGA AGGAAGTGAG GCCAATGAAG AACTGCGGCA GAAATTTGAG 1020
AGGGCCAAGA TCAGTCAGGG AACCAAGGTC CCGGAAGAAA AGACGACCAA CACTGTCTCC 1080
AAATTTGACA CAATGGCAA CAGAGACCGG ATGAAACTGA CCGATTTTAA CTTCCTAATG 1140
GTGCTGGGGA AAGGCAGCTT TGGCAAGGTC ATGCTTTCAG AACGAAAAGG CACAGATGAG 1200
CTCTATGCTG TGAAGATCCT GAAGAAGGAC GTTGTGATCC AAGATGATGA CGTGGAGTGC 1260
ACTATGGTGG AGAAGCGGGT GTTGGCCCTG CCTGGGAAGC CGCCCTTCCT GACCCAGCTC 1320
CACTCCTGCT TCCAGACCAT GGACCGCCTG TACTTTGTGA TGGAGTACGT GAATGGGGGC 1380
GACCTCATGT ATCACATCCA GCAAGTCGGC CGGTTCAAGG AGCCCCATGC TGTATTTTAC 1440
GCTGCAGAAA TTGCCATCGG TCTGTTCTTC TTACAGAGTA AGGGCATCAT TTACCGTGAC 1500
CTAAAACTTG ACAACGTGAT GCTCGATTCT GAGGGACACA TCAAGATTGC CGATTTTGGC 1560
ATGTGTAAGG AAAACATCTG GATGGGGTG ACAACCAAGA CATTCTGTGG CACTCCAGAC 1620
TACATCGCCC CCGAGATAAT TGCTTATCAG CCCTATGGGA AGTCCGTGGA TTGGTGGGCA 1680
TTTGGAGTCC TGCTGTATGA AATGTTGGCT GGGCAGGCAC CCTTTGAAGG GGAGGATGAA 1740
GATGAACTCT TCCAATCCAT CATGGAACAC AACGTAGCCT ATCCCAAGTC TATGTCCAAG 1800
GAAGCTGTGG CCATCTGCAA AGGGCTGATG ACCAAACACC CAGGCAAACG TCTGGGTTGT 1860
GGACCTGAAG GCGAACGTGA TATCAAAGAG CATGCATTTT TCCGGTATAT TGATTGGGAG 1920
AAACTTGAAC GCAAAGAGAT CCAGCCCCCT TATAAGCCAA AAGCTTGTGG GCGAAATGCT 1980
GAAAACTTCG ACCGATTTTT CACCCGCCAT CCACCAGTCC TAACACCTCC CGACCAGGAA 2040
GTCATCAGGA ATATTGACCA ATCAGAATTC GAAGGATTTT CCTTTGTTAA CTCTGAATTT 2100
TTAAAACCCG AAGTCAAGAG CTAA                                        2124
```

(SEQ ID NO:7)

FIG. 8

```
MAGSDTAPFL SQADDPDDGP VPGTPGLPGS TGNPKSEEPE VPDQEGLQRI TGLSPGRSAL  60
IVAVLCYINL LNYMDRFTVA GVLPDIEQFF NIGDSSSGLI QTVCCFVVHK RCHEFVTFSC 120
PGADKGPASD DPRSKHKFKI HTYSSPTFCD HCGSLLYGLI HQGMKCDTCM MNVHKRCVMN 180
VPSLCGTDHT ERRGRIYIQA HIDRDVLIVL VRDAKNLVPM DPNGLSDPYV KLKLIPDPKS 240
ESKQKTKTIK CSLNPEWNET FRFQLKESDK DRRLSVEIWD WDLTSRNDFM GSLSFGISEL 300
QKASVDGWFK LLSQEEGEYF NVPVPPEGSE ANEELRQKFE RAKISQGTKV PEEKTTNTVS 360
KFDNNGNRDR MKLTDFNFLM VLGKGSFGKV MLSERKGTDE LYAVKILKKD VVIQDDDVEC 420
TMVEKRVLAL PGKPPFLTQL HSCFQTMDRL YFVMEYVNGG DLMYHIQQVG RFKEPHAVFY 480
AAEIAIGLFF LQSKGIIYRD LKLDNVMLDS EGHIKIADFG MCKENIWDGV TTKTFCGTPD 540
YIAPEIIAYQ PYGKSVDWWA FGVLLYEMLA GQAPFEGEDE DELFQSIMEH NVAYPKSMSK 600
EAVAICKGLM TKHPGKRLGC GPEGERDIKE HAFFRYIDWE KLERKEIQPP YKPKACGRNA 660
ENFDRFFTRH PPVLTPPDQE VIRNIDQSEF EGFSFVNSEF LKPEVKS             707
```

(SEQ ID NO:8)

SEQUENCE LISTING

```
<160> NUMBER OF SEQ ID NOS: 8

<210> SEQ ID NO 1
<211> LENGTH: 2934
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
atgaacaaac tgtatatcgg aaacctcagc gagaacgccg ccccctcgga cctagaaagt        60
atcttcaagg acgccaagat cccggtgtcg ggacccttcc tggtgaagac tggctacgcg       120
```

```
ttcgtggact gcccggacga gagctgggcc ctcaaggcca tcgaggcgct ttcaggtaaa    180
atagaactgc acgggaaacc catagaagtt gagcactcgg tcccaaaaag gcaaaggatt    240
cggaaacttc agatacgaaa tatcccgcct catttacagt gggaggtgct ggatagttta    300
ctagtccagt atggagtggt ggagagctgt gagcaagtga acactgactc ggaaactgca    360
gttgtaaatg taacctattc cagtaaggac caagctagac aagcactaga caaactgaat    420
ggatttcagt tagagaattt caccttgaaa gtagcctata tccctgatga aatggccgcc    480
cagcaaaacc ccttgcagca gccccgaggt cgccgggggc ttgggcagag gggctcctca    540
aggcaggggt ctccaggatc cgtatccaag cagaaaccat gtgatttgcc tctgcgcctg    600
ctggttccca cccaatttgt tggagccatc ataggaaaag aaggtgccac cattcggaac    660
atcaccaaac agacccagtc taaaatcgat gtccaccgta aagaaaatgc ggggctgct    720 gagaagtcga ttactatcct ctctactcct gaaggcacct ctgcggcttg taagtctatt    780
ctggagatta tgcataagga agctcaagat ataaaattca cagaagagat cccttgaag    840 attttagctc ataataactt tgttggacgt cttattggta agaaggaag aaatcttaaa    900 aaaattgagc aagacacaga cactaaaatc acgatatctc cattgcagga attgacgctg    960
tataatccag aacgcactat tacagttaaa ggcaatgttg agacatgtgc caaagctgag   1020
gaggagatca tgaagaaaat cagggagtct tatgaaaatg atattgcttc tatgaatctt   1080
caagcacatt taattcctgg attaaatctg aacgccttgg gtctgttccc acccacttca   1140
gggatgccac ctcccacctc agggccccct tcagccatga ctcctcccta cccgcagttt   1200
gaggacccca ggagcaagca caagttcaaa atccacactt acggaagccc caccttctgc   1260
gatcactgtg ggtcactgct ctatggactt atccatcaag ggatgaaatg tgacacctgc   1320
gatatgaacg ttcacaagca atgcgtcatc aatgtcccca gcctctgcgg aatggatcac   1380
actgagaaga gggggcggat ttacctaaag gctgaggttg ctgatgaaaa gctccatgtc   1440
acagtacgag atgcaaaaaa tctaatccct atggatccaa acgggctttc agatccttat   1500
gtgaagctga aacttattcc tgatcccaag aatgaaagca agcaaaaaac caaaccatc    1560 cgctccacac taaatccgca gtggaatgag tcctttacat tcaaattgaa accttcagac   1620
aaagaccgac gactgtctgt agaaatctgg gactgggatc gaacaacaag gaatgacttc   1680
atgggatccc tttccttttgg agtttcggag ctgatgaaga tgccggccag tggatggtac   1740
aagttgctta ccaagaaga aggtgagtac tacaacgtac ccattccgga aggggacgag   1800
gaaggaaaca tggaactcag gcagaaattc gagaaagcca acttggcccc tgctggcaac   1860
aaagtcatca gtccctctga agacaggaaa caaccttcca caaccttga ccgagtgaaa   1920 ctcacggact tcaatttcct catggtgttg ggaaggggga gttttggaaa ggtgatgctt   1980
gccgacagga agggcacaga agaactgtat gcaatcaaaa tcctgaagaa ggatgtggtg   2040
attcaggatg atgacgtgga gtgcaccatg gtagaaaagc gagtcttggc cctgcttgac   2100 aaaccccgt tcttgacgca gctgcactcc tgcttccaga cagtggatcg gctgtacttc   2160
gtcatggaat atgtcaacgg tggggacctc atgtaccaca ttcagcaagt aggaaaattt   2220
aaggaaccac aagcagtatt ctatgcggca gagatttcca tcggattgtt ctttcttcat   2280
aaaagaggaa tcatttatag ggatctgaag ttagataacg tcatgttgga ttcagaagga   2340
catatcaaaa ttgctgactt tgggatgtgc aaggaacaca tgatggatgg agtcacgacc   2400
aggaccttct gtgggactcc agattatatc gccccagaga taatcgctta tcagccgtat   2460
```

```
ggaaaatctg tggactggtg ggcctatggc gtcctgttgt atgaaatgct tgccgggcag    2520
cctccatttg atggtgaaga tgaagacgag ctatttcagt ctatcatgga gcacaacgtt    2580
tcctatccaa aatccttgtc caaggaggct gtttctatct gcaaaggact gatgaccaaa    2640
cacccagcca agcggctggg ctgtgggcct gaggggagag gggacgtgag agagcatgcc    2700
ttcttccgga ggatcgactg ggaaaaactg gagaacaggg agatccagcc accattcaag    2760
cccaaagtgt gtggcaaagg agcagagaac tttgacaagt tcttcacacg aggacagccc    2820
gtcttaacac cacctgatca gctggttatt gctaacatag accagtctga ttttgaaggg    2880
ttctcgtatg tcaacccccca gtttgtgcac cccatcttac agagtgcagt atga          2934
```

<210> SEQ ID NO 2
<211> LENGTH: 977
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Met Asn Lys Leu Tyr Ile Gly Asn Leu Ser Glu Asn Ala Ala Pro Ser
1               5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Met Ala Ala
145                 150                 155                 160

Gln Gln Asn Pro Leu Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
            260                 265                 270
```

```
Phe Thr Glu Glu Ile Pro Leu Lys Ile Leu Ala His Asn Asn Phe Val
        275                 280                 285

Gly Arg Leu Ile Gly Lys Glu Gly Arg Asn Leu Lys Lys Ile Glu Gln
290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
            355                 360                 365

Asn Leu Asn Ala Leu Gly Leu Phe Pro Pro Thr Ser Gly Met Pro Pro
370                 375                 380

Pro Thr Ser Gly Pro Pro Ser Ala Met Thr Pro Pro Tyr Pro Gln Phe
385                 390                 395                 400

Glu Asp Pro Arg Ser Lys His Lys Phe Lys Ile His Thr Tyr Gly Ser
                405                 410                 415

Pro Thr Phe Cys Asp His Cys Gly Ser Leu Leu Tyr Gly Leu Ile His
            420                 425                 430

Gln Gly Met Lys Cys Asp Thr Cys Asp Met Asn Val His Lys Gln Cys
            435                 440                 445

Val Ile Asn Val Pro Ser Leu Cys Gly Met Asp His Thr Glu Lys Arg
            450                 455                 460

Gly Arg Ile Tyr Leu Lys Ala Glu Val Ala Asp Glu Lys Leu His Val
465                 470                 475                 480

Thr Val Arg Asp Ala Lys Asn Leu Ile Pro Met Asp Pro Asn Gly Leu
                485                 490                 495

Ser Asp Pro Tyr Val Lys Leu Lys Leu Ile Pro Asp Pro Lys Asn Glu
                500                 505                 510

Ser Lys Gln Lys Thr Lys Thr Ile Arg Ser Thr Leu Asn Pro Gln Trp
            515                 520                 525

Asn Glu Ser Phe Thr Phe Lys Leu Lys Pro Ser Asp Lys Asp Arg Arg
530                 535                 540

Leu Ser Val Glu Ile Trp Asp Trp Asp Arg Thr Thr Arg Asn Asp Phe
545                 550                 555                 560

Met Gly Ser Leu Ser Phe Gly Val Ser Glu Leu Met Lys Met Pro Ala
                565                 570                 575

Ser Gly Trp Tyr Lys Leu Leu Asn Gln Glu Glu Gly Glu Tyr Tyr Asn
            580                 585                 590

Val Pro Ile Pro Glu Gly Asp Glu Gly Asn Met Glu Leu Arg Gln
            595                 600                 605

Lys Phe Glu Lys Ala Lys Leu Gly Pro Ala Gly Asn Lys Val Ile Ser
610                 615                 620

Pro Ser Glu Asp Arg Lys Gln Pro Ser Asn Asn Leu Asp Arg Val Lys
625                 630                 635                 640

Leu Thr Asp Phe Asn Phe Leu Met Val Leu Gly Lys Gly Ser Phe Gly
                645                 650                 655

Lys Val Met Leu Ala Asp Arg Lys Gly Thr Glu Glu Leu Tyr Ala Ile
            660                 665                 670

Lys Ile Leu Lys Lys Asp Val Val Ile Gln Asp Asp Val Glu Cys
            675                 680                 685

Thr Met Val Glu Lys Arg Val Leu Ala Leu Leu Asp Lys Pro Pro Phe
```

```
                690                 695                 700
Leu Thr Gln Leu His Ser Cys Phe Gln Thr Val Asp Arg Leu Tyr Phe
705                 710                 715                 720

Val Met Glu Tyr Val Asn Gly Gly Asp Leu Met Tyr His Ile Gln Gln
                725                 730                 735

Val Gly Lys Phe Lys Glu Pro Gln Ala Val Phe Tyr Ala Ala Glu Ile
                740                 745                 750

Ser Ile Gly Leu Phe Phe Leu His Lys Arg Gly Ile Ile Tyr Arg Asp
                755                 760                 765

Leu Lys Leu Asp Asn Val Met Leu Asp Ser Glu Gly His Ile Lys Ile
770                 775                 780

Ala Asp Phe Gly Met Cys Lys Glu His Met Met Asp Gly Val Thr Thr
785                 790                 795                 800

Arg Thr Phe Cys Gly Thr Pro Asp Tyr Ile Ala Pro Glu Ile Ile Ala
                805                 810                 815

Tyr Gln Pro Tyr Gly Lys Ser Val Asp Trp Ala Tyr Gly Val Leu
                820                 825                 830

Leu Tyr Glu Met Leu Ala Gly Gln Pro Pro Phe Asp Gly Glu Asp Glu
                835                 840                 845

Asp Glu Leu Phe Gln Ser Ile Met Glu His Asn Val Ser Tyr Pro Lys
850                 855                 860

Ser Leu Ser Lys Glu Ala Val Ser Ile Cys Lys Gly Leu Met Thr Lys
865                 870                 875                 880

His Pro Ala Lys Arg Leu Gly Cys Gly Pro Glu Gly Glu Arg Asp Val
                885                 890                 895

Arg Glu His Ala Phe Phe Arg Arg Ile Asp Trp Glu Lys Leu Glu Asn
                900                 905                 910

Arg Glu Ile Gln Pro Pro Phe Lys Pro Lys Val Cys Gly Lys Gly Ala
                915                 920                 925

Glu Asn Phe Asp Lys Phe Phe Thr Arg Gly Gln Pro Val Leu Thr Pro
                930                 935                 940

Pro Asp Gln Leu Val Ile Ala Asn Ile Asp Gln Ser Asp Phe Glu Gly
945                 950                 955                 960

Phe Ser Tyr Val Asn Pro Gln Phe Val His Pro Ile Leu Gln Ser Ala
                965                 970                 975

Val

<210> SEQ ID NO 3
<211> LENGTH: 1629
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
atgtttcgga atagtctcaa gatgctgctt actggtggga atcaagtcg taaaaacagg      60 tcaagtgatg gagggagcga ggaaccaccg gatcgaagac agtcaagtgt agactctcgc     120
caaagccgct ctgggcaagt acgagatgca aaaaatctaa tccctatgga tccaaacggg    180
ctttcagatc cttatgtgaa gctgaaactt attcctgatc caagaatga aagcaagcaa     240 aaaaccaaaa ccatccgctc cacactaaat ccgcagtgga atgagtcctt acattcaaa    300 ttgaaacctt cagacaaaga ccgacgactg tctgtagaaa tctgggactg ggatcgaaca    360
```

```
acaaggaatg acttcatggg atcccttttcc tttggagttt cggagctgat gaagatgccg   420
gccagtggat ggtacaagtt gcttaaccaa gaagaaggtg agtactacaa cgtacccatt   480
ccggaagggg acgaggaagg aaacatggaa ctcaggcaga aattcgagaa agccaaactt   540
ggccctgctg caacaaagt catcagtccc tctgaagaca ggaaacaacc ttccaacaac   600
cttgaccgag tgaaactcac ggacttcaat ttcctcatgg tgttgggaaa ggggagtttt   660
ggaaaggtga tgcttgccga caggaagggc acagaagaac tgtatgcaat caaaatcctg   720
aagaaggatg tggtgattca ggatgatgac gtggagtgca ccatggtaga aaagcgagtc   780
ttggccctgc ttgacaaacc cccgttcttg acgcagctgc actcctgctt ccagacagtg   840
gatcggctgt acttcgtcat ggaatatgtc aacggtgggg acctcatgta ccacattcag   900
caagtaggaa aatttaagga accacaagca gtattctatg cggcagagat ttccatcgga   960
ttgttctttc ttcataaaag aggaatcatt tatagggatc tgaagttaga taacgtcatg  1020
ttggattcag aaggacatat caaaattgct gactttggga tgtgcaagga acacatgatg  1080
gatggagtca cgaccaggac cttctgtggg actccagatt atatcgcccc agagataatc  1140
gcttatcagc cgtatggaaa atctgtggac tggtgggcct atgcgtcct gttgtatgaa   1200
atgcttgccg ggcagcctcc atttgatggt gaagatgaag cgagctatt tcagtctatc   1260
atggagcaca acgtttccta tccaaaatcc ttgtccaagg aggctgtttc tatctgcaaa  1320
ggactgatga ccaaacaccc agccaagcgg ctgggctgtg ggcctgaggg ggagagggac  1380
gtgagagagc atgccttctt ccggaggatc gactgggaaa aactggagaa cagggagatc  1440
cagccaccat tcaagcccaa agtgtgtggc aaaggagcag agaactttga caagttcttc  1500
acacgaggac agcccgtctt aacaccacct gatcagctgg ttattgctaa catagaccag  1560
tctgattttg aagggttctc gtatgtcaac ccccagtttg tgcacccatt cttacagagt  1620
gcagtatga                                                         1629
```

<210> SEQ ID NO 4
<211> LENGTH: 542
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

```
Met Phe Arg Asn Ser Leu Lys Met Leu Leu Thr Gly Gly Lys Ser Ser
1               5                   10                  15

Arg Lys Asn Arg Ser Ser Asp Gly Gly Ser Glu Glu Pro Pro Asp Arg
            20                  25                  30

Arg Gln Ser Ser Val Asp Ser Arg Gln Ser Arg Ser Gly Gln Val Arg
        35                  40                  45

Asp Ala Lys Asn Leu Ile Pro Met Asp Pro Asn Gly Leu Ser Asp Pro
    50                  55                  60

Tyr Val Lys Leu Lys Leu Ile Pro Asp Pro Lys Asn Glu Ser Lys Gln
65                  70                  75                  80

Lys Thr Lys Thr Ile Arg Ser Thr Leu Asn Pro Gln Trp Asn Glu Ser
                85                  90                  95

Phe Thr Phe Lys Leu Lys Pro Ser Asp Lys Asp Arg Arg Leu Ser Val
            100                 105                 110

Glu Ile Trp Asp Trp Asp Arg Thr Thr Arg Asn Asp Phe Met Gly Ser
        115                 120                 125
```

```
Leu Ser Phe Gly Val Ser Glu Leu Met Lys Met Pro Ala Ser Gly Trp
    130                 135                 140
Tyr Lys Leu Leu Asn Gln Glu Glu Gly Glu Tyr Tyr Asn Val Pro Ile
145                 150                 155                 160
Pro Glu Gly Asp Glu Glu Gly Asn Met Glu Leu Arg Gln Lys Phe Glu
                165                 170                 175
Lys Ala Lys Leu Gly Pro Ala Gly Asn Lys Val Ile Ser Pro Ser Glu
                180                 185                 190
Asp Arg Lys Gln Pro Ser Asn Asn Leu Asp Arg Val Lys Leu Thr Asp
            195                 200                 205
Phe Asn Phe Leu Met Val Leu Gly Lys Gly Ser Phe Gly Lys Val Met
    210                 215                 220
Leu Ala Asp Arg Lys Gly Thr Glu Glu Leu Tyr Ala Ile Lys Ile Leu
225                 230                 235                 240
Lys Lys Asp Val Val Ile Gln Asp Asp Asp Val Glu Cys Thr Met Val
                245                 250                 255
Glu Lys Arg Val Leu Ala Leu Leu Asp Lys Pro Pro Phe Leu Thr Gln
                260                 265                 270
Leu His Ser Cys Phe Gln Thr Val Asp Arg Leu Tyr Phe Val Met Glu
    275                 280                 285
Tyr Val Asn Gly Gly Asp Leu Met Tyr His Ile Gln Gln Val Gly Lys
290                 295                 300
Phe Lys Glu Pro Gln Ala Val Phe Tyr Ala Ala Glu Ile Ser Ile Gly
305                 310                 315                 320
Leu Phe Phe Leu His Lys Arg Gly Ile Ile Tyr Arg Asp Leu Lys Leu
                325                 330                 335
Asp Asn Val Met Leu Asp Ser Glu Gly His Ile Lys Ile Ala Asp Phe
                340                 345                 350
Gly Met Cys Lys Glu His Met Met Asp Gly Val Thr Thr Arg Thr Phe
            355                 360                 365
Cys Gly Thr Pro Asp Tyr Ile Ala Pro Glu Ile Ile Ala Tyr Gln Pro
    370                 375                 380
Tyr Gly Lys Ser Val Asp Trp Trp Ala Tyr Gly Val Leu Leu Tyr Glu
385                 390                 395                 400
Met Leu Ala Gly Gln Pro Pro Phe Asp Gly Glu Asp Glu Asp Glu Leu
                405                 410                 415
Phe Gln Ser Ile Met Glu His Asn Val Ser Tyr Pro Lys Ser Leu Ser
                420                 425                 430
Lys Glu Ala Val Ser Ile Cys Lys Gly Leu Met Thr Lys His Pro Ala
            435                 440                 445
Lys Arg Leu Gly Cys Gly Pro Glu Gly Glu Arg Asp Val Arg Glu His
    450                 455                 460
Ala Phe Phe Arg Arg Ile Asp Trp Glu Lys Leu Glu Asn Arg Glu Ile
465                 470                 475                 480
Gln Pro Pro Phe Lys Pro Lys Val Cys Gly Lys Gly Ala Glu Asn Phe
                485                 490                 495
Asp Lys Phe Phe Thr Arg Gly Gln Pro Val Leu Thr Pro Pro Asp Gln
                500                 505                 510
Leu Val Ile Ala Asn Ile Asp Gln Ser Asp Phe Glu Gly Phe Ser Tyr
            515                 520                 525
Val Asn Pro Gln Phe Val His Pro Ile Leu Gln Ser Ala Val
    530                 535                 540
```

<210> SEQ ID NO 5
<211> LENGTH: 3510
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5

```
atggcttccc cacccccacca gcagctgctg catcaccaca gcaccgaggt gagctgcgac      60
tccagcgggg acagcaacag cgtgcgcgtc aagatcaacc ccaagcagct gtcctccaac     120
agccacccca agcactgcaa atacagcatc tcctctagct gcagcagctc tggggactcc     180
ggggggcgtcc cccggcgagt gggcggcgga ggccggctgc gcaggcagaa gaagctgccc     240
cagctgttcg agagggcctc cagccgctgg tgggaccccca agttcgactc ggtgaacctg     300
gaggaggcct gcctggagcg ctgcttcccg cagacccagc gccggttccg gtatgcgctc     360
ttctacatcg gcttcgcctg ccttctgtgg agcatctatt tgcggtcca catgagatcc     420
agactgatcg tcatggtcgc ccccgcgctg tgcttcctcc tggtgtgtgt gggcttcttt     480
ctgtttacct tcaccaagct gtacgcccgg cattacgcgt ggacctcgct ggctctcacc     540
ctgctggtgt cgccctgac cctggctgcg cagttccagg tcttgacgcc tgtctcagga     600
cgcggcgaca gctccaacct tacgccaca gcccggccca cagatacttg cttatctcaa     660
gtggggagct ctccatgtg catcgaagtg ctcttttttgc tctataccgt catgcactta     720
cctttgtacc tgagtttgtg tctgggggtg gcctactctg tccttttcga gacctttggc     780
taccatttcc gggatgaagc ctgcttcccc tcgcccggag ccggggccct gcactgggag     840
ctgctgagca gggggctgct ccacggctgc atccacgcca tcgggtcca cctgttcgtc     900
atgtcccagg tgaggtccag gagcaccttc ctcaaggtgg ggcaatccat tatgcacggg     960
aaggacctgg aagtggaaaa agccctcaaa gagaggatga ttcattccgt gatgccaaga    1020
atcatagccg atgacttaat gaagcaggga gatgaggaga gtgagaattc tgtcaagagg    1080
catgccacct cgagccccaa gaacaggaag aaaaagtctt ccatccaaaa agctcctata    1140
gccttccgcc ttttaagat gcagcagatc gaagaagtca gtatttttatt tgcagatatc    1200
gtgggcttca ccaagatgag tgccaacaag tctgcccacg ccctggtggg tctcctgaac    1260
gatctgttcg gtcgcttcga ccgcctgtgt gaggagacca agtgtgagaa aatcagcacc    1320
ctgggagact gttactactg cgtggcgggc tgtcccgagc ccggggccga ccatgcctac    1380
tgctgcatcg agatgggcct gggcatgatc aaggccatcg agcagttctg ccaggagaag    1440
aaggagatgg tgaacatgag agtcggggtg cacacgggca ccgtcctttg cggcatcctg    1500
ggcatgagga ggtttaaatt tgacgtgtgg tccaacgatg tgaacctggc caatctcatg    1560
gagcagctgg gagtggccgg caaagttcac atttctgagg ccaccgcaaa atacttagat    1620
gaccggtacg aaatggaaga tgggaaagtt attgaacggc tgggccagag cgtggttgct    1680
gaccagttga agtttgctg ctttgtggtg cacaagcggt gccatgaatt tgtcacattc    1740
tcctgccctg cgctgacaa gggtccagcc tccgatgacc cccgcagcaa acacaagttt    1800
aagatccaca cgtactccag ccccacgttt tgtgaccact gtgggtcact gctgtatgga    1860
ctcatccacc aggggatgaa atgtgacacc tgcatgatga atgtgcacaa gcgctgcgtg    1920
atgaatgttc ccagcctgtg tggcacggac cacacggagc gccgcggccg catctacatc    1980
caggcccaca tcgacaggga cgtcctcatt gtcctcgtaa gagatgctaa aaaccttgta    2040
```

```
cctatggacc ccaatggcct gtcagatccc tacgtaaaac tgaaactgat tcccgatccc    2100
aaaagtgaga gcaaacagaa gaccaaaacc atcaaatgct ccctcaaccc tgagtggaat    2160
gagacattta gatttcagct gaaagaatcg gacaaagaca gaagactgtc agtagagatt    2220
tgggattggg atttgaccag caggaatgac ttcatgggga ctttgtcctt tgggatttct    2280
gaacttcaga aagccagtgt tgatggctgg tttaagttac tgagccagga ggaaggcgag    2340
tacttcaatg tgcctgtgcc accagaagga agtgaggcca atgaagaact gcggcagaaa    2400
tttgagaggg ccaagatcag tcagggaacc aaggtcccgg aagaaaagac gaccaacact    2460
gtctccaaat tgacaacaa tggcaacaga gaccggatga aactgaccga ttttaacttc    2520
ctaatggtgc tggggaaagg cagctttggc aaggtcatgc tttcagaacg aaaaggcaca    2580
gatgagctct atgctgtgaa gatcctgaag aaggacgttg tgatccaaga tgatgacgtg    2640
gagtgcacta tggtggagaa gcgggtgttg gccctgcctg ggaagccgcc cttcctgacc    2700
cagctccact cctgcttcca gaccatggac cgcctgtact ttgtgatgga gtacgtgaat    2760
gggggcgacc tcatgtatca catccagcaa gtcggccggt tcaaggagcc ccatgctgta    2820
ttttacgctg cagaaattgc catcggtctg ttcttcttac agagtaaggg catcatttac    2880
cgtgacctaa aacttgacaa cgtgatgctc gattctgagg acacatcaa gattgccgat    2940 tttggcatgt gtaaggaaaa catctgggat ggggtgacaa ccaagacatt ctgtggcact    3000
ccagactaca tcgcccccga gataattgct tatcagccct atgggaagtc cgtggattgg    3060
tgggcatttg gagtcctgct gtatgaaatg ttggctgggc aggcacccct tgaaggggag    3120
gatgaagatg aactcttcca atccatcatg gaacacaacg tagcctatcc caagtctatg    3180
tccaaggaag ctgtggccat ctgcaaaggg ctgatgacca acacccagg caaacgtctg    3240 ggttgtggac ctgaaggcga acgtgatatc aaagagcatg cattttttccg gtatattgat    3300 tgggagaaac ttgaacgcaa agagatccag ccccccttata agccaaaagc ttgtgggcga    3360
aatgctgaaa acttcgaccg attttttcacc cgccatccac cagtcctaac acctcccgac    3420
caggaagtca tcaggaatat tgaccaatca gaattcgaag gattttcctt tgttaactct    3480 gaattttttaa aacccgaagt caagagctaa                                   3510
```

<210> SEQ ID NO 6
<211> LENGTH: 1169
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Met Ala Ser Pro Pro His Gln Gln Leu Leu His His Ser Thr Glu
1               5                   10                  15

Val Ser Cys Asp Ser Ser Gly Asp Ser Asn Ser Val Arg Val Lys Ile
                20                  25                  30

Asn Pro Lys Gln Leu Ser Ser Asn Ser His Pro Lys His Cys Lys Tyr
            35                  40                  45

Ser Ile Ser Ser Ser Cys Ser Ser Gly Asp Ser Gly Gly Val Pro
        50                  55                  60

Arg Arg Val Gly Gly Gly Arg Leu Arg Arg Gln Lys Lys Leu Pro
65                  70                  75                  80

Gln Leu Phe Glu Arg Ala Ser Ser Arg Trp Trp Asp Pro Lys Phe Asp

```
                    85                  90                  95
Ser Val Asn Leu Glu Glu Ala Cys Leu Glu Arg Cys Phe Pro Gln Thr
                100                 105                 110

Gln Arg Arg Phe Arg Tyr Ala Leu Phe Tyr Ile Gly Phe Ala Cys Leu
                115                 120                 125

Leu Trp Ser Ile Tyr Phe Ala Val His Met Arg Ser Arg Leu Ile Val
            130                 135                 140

Met Val Ala Pro Ala Leu Cys Phe Leu Val Cys Val Gly Phe Phe
145                 150                 155                 160

Leu Phe Thr Phe Thr Lys Leu Tyr Ala Arg His Tyr Ala Trp Thr Ser
                165                 170                 175

Leu Ala Leu Thr Leu Leu Val Phe Ala Leu Thr Leu Ala Ala Gln Phe
            180                 185                 190

Gln Val Leu Thr Pro Val Ser Gly Arg Gly Asp Ser Ser Asn Leu Thr
                195                 200                 205

Ala Thr Ala Arg Pro Thr Asp Thr Cys Leu Ser Gln Val Gly Ser Phe
            210                 215                 220

Ser Met Cys Ile Glu Val Leu Phe Leu Leu Tyr Thr Val Met His Leu
225                 230                 235                 240

Pro Leu Tyr Leu Ser Leu Cys Leu Gly Val Ala Tyr Ser Val Leu Phe
                245                 250                 255

Glu Thr Phe Gly Tyr His Phe Arg Asp Glu Ala Cys Phe Pro Ser Pro
            260                 265                 270

Gly Ala Gly Ala Leu His Trp Glu Leu Leu Ser Arg Gly Leu Leu His
            275                 280                 285

Gly Cys Ile His Ala Ile Gly Val His Leu Phe Val Met Ser Gln Val
            290                 295                 300

Arg Ser Arg Ser Thr Phe Leu Lys Val Gly Gln Ser Ile Met His Gly
305                 310                 315                 320

Lys Asp Leu Glu Val Glu Lys Ala Leu Lys Glu Arg Met Ile His Ser
                325                 330                 335

Val Met Pro Arg Ile Ile Ala Asp Asp Leu Met Lys Gln Gly Asp Glu
            340                 345                 350

Glu Ser Glu Asn Ser Val Lys Arg His Ala Thr Ser Ser Pro Lys Asn
            355                 360                 365

Arg Lys Lys Lys Ser Ser Ile Gln Lys Ala Pro Ile Ala Phe Arg Pro
            370                 375                 380

Phe Lys Met Gln Gln Ile Glu Glu Val Ser Ile Leu Phe Ala Asp Ile
385                 390                 395                 400

Val Gly Phe Thr Lys Met Ser Ala Asn Lys Ser Ala His Ala Leu Val
                405                 410                 415

Gly Leu Leu Asn Asp Leu Phe Gly Arg Phe Asp Arg Leu Cys Glu Glu
            420                 425                 430

Thr Lys Cys Glu Lys Ile Ser Thr Leu Gly Asp Cys Tyr Tyr Cys Val
            435                 440                 445

Ala Gly Cys Pro Glu Pro Arg Ala Asp His Ala Tyr Cys Cys Ile Glu
            450                 455                 460

Met Gly Leu Gly Met Ile Lys Ala Ile Glu Gln Phe Cys Gln Glu Lys
465                 470                 475                 480

Lys Glu Met Val Asn Met Arg Val Gly Val His Thr Gly Thr Val Leu
                485                 490                 495

Cys Gly Ile Leu Gly Met Arg Arg Phe Lys Phe Asp Val Trp Ser Asn
            500                 505                 510
```

-continued

```
Asp Val Asn Leu Ala Asn Leu Met Glu Gln Leu Gly Val Ala Gly Lys
            515                 520                 525

Val His Ile Ser Glu Ala Thr Ala Lys Tyr Leu Asp Asp Arg Tyr Glu
        530                 535                 540

Met Glu Asp Gly Lys Val Ile Glu Arg Leu Gly Gln Ser Val Val Ala
545                 550                 555                 560

Asp Gln Leu Lys Val Cys Cys Phe Val His Lys Arg Cys His Glu
                565                 570                 575

Phe Val Thr Phe Ser Cys Pro Gly Ala Asp Lys Gly Pro Ala Ser Asp
                580                 585                 590

Asp Pro Arg Ser Lys His Lys Phe Lys Ile His Thr Tyr Ser Ser Pro
            595                 600                 605

Thr Phe Cys Asp His Cys Gly Ser Leu Leu Tyr Gly Leu Ile His Gln
        610                 615                 620

Gly Met Lys Cys Asp Thr Cys Met Met Asn Val His Lys Arg Cys Val
625                 630                 635                 640

Met Asn Val Pro Ser Leu Cys Gly Thr Asp His Thr Glu Arg Arg Gly
                645                 650                 655

Arg Ile Tyr Ile Gln Ala His Ile Asp Arg Asp Val Leu Ile Val Leu
            660                 665                 670

Val Arg Asp Ala Lys Asn Leu Val Pro Met Asp Pro Asn Gly Leu Ser
        675                 680                 685

Asp Pro Tyr Val Lys Leu Lys Leu Ile Pro Asp Pro Lys Ser Glu Ser
        690                 695                 700

Lys Gln Lys Thr Lys Thr Ile Lys Cys Ser Leu Asn Pro Glu Trp Asn
705                 710                 715                 720

Glu Thr Phe Arg Phe Gln Leu Lys Glu Ser Asp Lys Asp Arg Arg Leu
                725                 730                 735

Ser Val Glu Ile Trp Asp Trp Asp Leu Thr Ser Arg Asn Asp Phe Met
            740                 745                 750

Gly Ser Leu Ser Phe Gly Ile Ser Glu Leu Gln Lys Ala Ser Val Asp
        755                 760                 765

Gly Trp Phe Lys Leu Leu Ser Gln Glu Glu Gly Glu Tyr Phe Asn Val
        770                 775                 780

Pro Val Pro Pro Glu Gly Ser Glu Ala Asn Glu Glu Leu Arg Gln Lys
785                 790                 795                 800

Phe Glu Arg Ala Lys Ile Ser Gln Gly Thr Lys Val Pro Glu Glu Lys
                805                 810                 815

Thr Thr Asn Thr Val Ser Lys Phe Asp Asn Asn Gly Asn Arg Asp Arg
            820                 825                 830

Met Lys Leu Thr Asp Phe Asn Phe Leu Met Val Leu Gly Lys Gly Ser
        835                 840                 845

Phe Gly Lys Val Met Leu Ser Glu Arg Lys Gly Thr Asp Glu Leu Tyr
        850                 855                 860

Ala Val Lys Ile Leu Lys Lys Asp Val Val Ile Gln Asp Asp Asp Val
865                 870                 875                 880

Glu Cys Thr Met Val Glu Lys Arg Val Leu Ala Leu Pro Gly Lys Pro
                885                 890                 895

Pro Phe Leu Thr Gln Leu His Ser Cys Phe Gln Thr Met Asp Arg Leu
            900                 905                 910

Tyr Phe Val Met Glu Tyr Val Asn Gly Gly Asp Leu Met Tyr His Ile
        915                 920                 925
```

Gln Gln Val Gly Arg Phe Lys Glu Pro His Ala Val Phe Tyr Ala Ala
    930             935                 940

Glu Ile Ala Ile Gly Leu Phe Phe Leu Gln Ser Lys Gly Ile Ile Tyr
945             950                 955                 960

Arg Asp Leu Lys Leu Asp Asn Val Met Leu Asp Ser Glu Gly His Ile
            965                 970                 975

Lys Ile Ala Asp Phe Gly Met Cys Lys Glu Asn Ile Trp Asp Gly Val
        980                 985                 990

Thr Thr Lys Thr Phe Cys Gly Thr Pro Asp Tyr Ile Ala Pro Glu Ile
    995                 1000                1005

Ile Ala Tyr Gln Pro Tyr Gly Lys Ser Val Asp Trp Trp Ala Phe
    1010            1015                1020

Gly Val Leu Leu Tyr Glu Met Leu Ala Gly Gln Ala Pro Phe Glu
    1025            1030            1035

Gly Glu Asp Glu Asp Glu Leu Phe Gln Ser Ile Met Glu His Asn
    1040            1045            1050

Val Ala Tyr Pro Lys Ser Met Ser Lys Glu Ala Val Ala Ile Cys
    1055            1060            1065

Lys Gly Leu Met Thr Lys His Pro Gly Lys Arg Leu Gly Cys Gly
    1070            1075            1080

Pro Glu Gly Glu Arg Asp Ile Lys Glu His Ala Phe Phe Arg Tyr
    1085            1090            1095

Ile Asp Trp Glu Lys Leu Glu Arg Lys Glu Ile Gln Pro Pro Tyr
    1100            1105            1110

Lys Pro Lys Ala Cys Gly Arg Asn Ala Glu Asn Phe Asp Arg Phe
    1115            1120            1125

Phe Thr Arg His Pro Pro Val Leu Thr Pro Pro Asp Gln Glu Val
    1130            1135            1140

Ile Arg Asn Ile Asp Gln Ser Glu Phe Glu Gly Phe Ser Phe Val
    1145            1150            1155

Asn Ser Glu Phe Leu Lys Pro Glu Val Lys Ser
    1160            1165

<210> SEQ ID NO 7
<211> LENGTH: 2124
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 7

```
atggccgggt ccgacaccgc gcccttcctc agccaggcgg atgacccgga cgacgggcca      60
gtgcctggca ccccggggtt gccagggtcc acggggaacc cgaagtccga ggagcccgag     120
gtcccggacc aggagggggct gcagcgcatc accggcctgt ctcccggccg ttcggctctc    180
atagtggcgg tgctgtgcta catcaatctc ctgaactaca tggaccgctt caccgtggct    240
ggcgtccttc ccgacatcga gcagttcttc aacatcgggg acagtagctc tgggctcatc    300
cagaccgttt gctgctttgt ggtgcacaag cggtgccatg aatttgtcac attctcctgc    360
cctggcgctg acaagggtcc agcctccgat gaccccgcca gcaaacacaa gtttaagatc    420
cacacgtact ccagccccac gttttgtgac actgtgggt cactgctgta tggactcatc    480
caccagggga tgaaatgtga cacctgcatg atgaatgtgc acaagcgctg cgtgatgaat    540
gttcccagcc tgtgtggcac ggaccacacg gagcgccgcg gccgcatcta catccaggcc    600
```

-continued

```
cacatcgaca gggacgtcct cattgtcctc gtaagagatg ctaaaaacct tgtacctatg    660
gaccccaatg gcctgtcaga tccctacgta aaactgaaac tgattcccga tcccaaaagt    720
gagagcaaac agaagaccaa aaccatcaaa tgctccctca accctgagtg aatgagaca     780 tttagatttc agctgaaaga atcggacaaa gacagaagac tgtcagtaga gatttgggat    840
tgggatttga ccagcaggaa tgacttcatg ggatctttgt cctttgggat ttctgaactt    900
cagaaagcca gtgttgatgg ctggtttaag ttactgagcc aggaggaagg cgagtacttc    960
aatgtgcctg tgccaccaga aggaagtgag gccaatgaag aactgcggca gaaatttgag   1020
agggccaaga tcagtcaggg aaccaaggtc ccggaagaaa agacgaccaa cactgtctcc   1080
aaatttgaca acaatggcaa cagagaccgg atgaaactga ccgattttaa cttcctaatg   1140
gtgctgggga aaggcagctt tggcaaggtc atgctttcag aacgaaaagg cacagatgag   1200
ctctatgctg tgaagatcct gaagaaggac gttgtgatcc aagatgatga cgtggagtgc   1260
actatggtgg agaagcgggt gttggccctg cctgggaagc cgcccttcct gacccagctc   1320
cactcctgct tccagaccat ggaccgcctg tactttgtga tggagtacgt gaatggggc    1380 gacctcatgt atcacatcca gcaagtcggc cggttcaagg agcccatgc tgtattttac    1440 gctgcagaaa ttgccatcgg tctgttcttc ttacagagta agggcatcat ttaccgtgac   1500
ctaaaacttg acaacgtgat gctcgattct gagggacaca tcaagattgc cgattttggc   1560
atgtgtaagg aaaacatctg ggatggggtg acaaccaaga cattctgtgg cactccagac   1620
tacatcgccc ccgagataat tgcttatcag ccctatggga agtccgtgga ttggtgggca   1680
tttggagtcc tgctgtatga aatgttggct gggcaggcac cctttgaagg ggaggatgaa   1740
gatgaactct tccaatccat catggaacac aacgtagcct atcccaagtc tatgtccaag   1800
gaagctgtgg ccatctgcaa agggctgatg accaaacacc caggcaaacg tctgggttgt   1860
ggacctgaag cgaacgtga tatcaaagag catgcatttt tccggtatat tgattgggag    1920
aaacttgaac gcaaagagat ccagccccct tataagccaa agcttgtgg gcgaaatgct   1980 gaaaacttcg accgattttt caccgcctt ccaccagtcc taacacctcc cgaccaggaa   2040
gtcatcagga atattgacca atcagaattc gaaggatttt cctttgttaa ctctgaattt   2100
ttaaaacccg aagtcaagag ctaa                                          2124
```

<210> SEQ ID NO 8
<211> LENGTH: 707
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Met Ala Gly Ser Asp Thr Ala Pro Phe Leu Ser Gln Ala Asp Pro
1               5                   10                  15

Asp Asp Gly Pro Val Pro Gly Thr Pro Gly Leu Pro Gly Ser Thr Gly
            20                  25                  30

Asn Pro Lys Ser Glu Glu Pro Glu Val Pro Asp Gln Glu Gly Leu Gln
        35                  40                  45

Arg Ile Thr Gly Leu Ser Pro Gly Arg Ser Ala Leu Ile Val Ala Val
    50                  55                  60

Leu Cys Tyr Ile Asn Leu Leu Asn Tyr Met Asp Arg Phe Thr Val Ala
65                  70                  75                  80
```

```
Gly Val Leu Pro Asp Ile Glu Gln Phe Phe Asn Ile Gly Asp Ser Ser
                85                  90                  95

Ser Gly Leu Ile Gln Thr Val Cys Cys Phe Val His Lys Arg Cys
            100                 105                 110

His Glu Phe Val Thr Phe Ser Cys Pro Gly Ala Asp Lys Gly Pro Ala
        115                 120                 125

Ser Asp Asp Pro Arg Ser Lys His Lys Phe Lys Ile His Thr Tyr Ser
    130                 135                 140

Ser Pro Thr Phe Cys Asp His Cys Gly Ser Leu Leu Tyr Gly Leu Ile
145                 150                 155                 160

His Gln Gly Met Lys Cys Asp Thr Cys Met Met Asn Val His Lys Arg
                165                 170                 175

Cys Val Met Asn Val Pro Ser Leu Cys Gly Thr Asp His Thr Glu Arg
                180                 185                 190

Arg Gly Arg Ile Tyr Ile Gln Ala His Ile Asp Arg Asp Val Leu Ile
            195                 200                 205

Val Leu Val Arg Asp Ala Lys Asn Leu Val Pro Met Asp Pro Asn Gly
        210                 215                 220

Leu Ser Asp Pro Tyr Val Lys Leu Lys Leu Ile Pro Asp Pro Lys Ser
225                 230                 235                 240

Glu Ser Lys Gln Lys Thr Lys Thr Ile Lys Cys Ser Leu Asn Pro Glu
                245                 250                 255

Trp Asn Glu Thr Phe Arg Phe Gln Leu Lys Glu Ser Asp Lys Asp Arg
            260                 265                 270

Arg Leu Ser Val Glu Ile Trp Asp Trp Asp Leu Thr Ser Arg Asn Asp
        275                 280                 285

Phe Met Gly Ser Leu Ser Phe Gly Ile Ser Glu Leu Gln Lys Ala Ser
    290                 295                 300

Val Asp Gly Trp Phe Lys Leu Leu Ser Gln Glu Gly Glu Tyr Phe
305                 310                 315                 320

Asn Val Pro Val Pro Pro Glu Gly Ser Glu Ala Asn Glu Glu Leu Arg
                325                 330                 335

Gln Lys Phe Glu Arg Ala Lys Ile Ser Gln Gly Thr Lys Val Pro Glu
            340                 345                 350

Glu Lys Thr Thr Asn Thr Val Ser Lys Phe Asp Asn Asn Gly Asn Arg
        355                 360                 365

Asp Arg Met Lys Leu Thr Asp Phe Asn Phe Leu Met Val Leu Gly Lys
    370                 375                 380

Gly Ser Phe Gly Lys Val Met Leu Ser Glu Arg Lys Gly Thr Asp Glu
385                 390                 395                 400

Leu Tyr Ala Val Lys Ile Leu Lys Lys Asp Val Val Ile Gln Asp Asp
                405                 410                 415

Asp Val Glu Cys Thr Met Val Glu Lys Arg Val Leu Ala Leu Pro Gly
            420                 425                 430

Lys Pro Pro Phe Leu Thr Gln Leu His Ser Cys Phe Gln Thr Met Asp
        435                 440                 445

Arg Leu Tyr Phe Val Met Glu Tyr Val Asn Gly Gly Asp Leu Met Tyr
    450                 455                 460

His Ile Gln Gln Val Gly Arg Phe Lys Glu Pro His Ala Val Phe Tyr
465                 470                 475                 480

Ala Ala Glu Ile Ala Ile Gly Leu Phe Phe Leu Gln Ser Lys Gly Ile
                485                 490                 495
```

-continued

```
Ile Tyr Arg Asp Leu Lys Leu Asp Asn Val Met Leu Asp Ser Glu Gly
            500                 505                 510

His Ile Lys Ile Ala Asp Phe Gly Met Cys Lys Glu Asn Ile Trp Asp
        515                 520                 525

Gly Val Thr Thr Lys Thr Phe Cys Gly Thr Pro Asp Tyr Ile Ala Pro
        530                 535                 540

Glu Ile Ile Ala Tyr Gln Pro Tyr Gly Lys Ser Val Asp Trp Trp Ala
545                 550                 555                 560

Phe Gly Val Leu Leu Tyr Glu Met Leu Ala Gly Gln Ala Pro Phe Glu
                565                 570                 575

Gly Glu Asp Glu Asp Glu Leu Phe Gln Ser Ile Met Glu His Asn Val
            580                 585                 590

Ala Tyr Pro Lys Ser Met Ser Lys Glu Ala Val Ala Ile Cys Lys Gly
        595                 600                 605

Leu Met Thr Lys His Pro Gly Lys Arg Leu Gly Cys Gly Pro Glu Gly
    610                 615                 620

Glu Arg Asp Ile Lys Glu His Ala Phe Phe Arg Tyr Ile Asp Trp Glu
625                 630                 635                 640

Lys Leu Glu Arg Lys Glu Ile Gln Pro Pro Tyr Lys Pro Lys Ala Cys
                645                 650                 655

Gly Arg Asn Ala Glu Asn Phe Asp Arg Phe Phe Thr Arg His Pro Pro
                660                 665                 670

Val Leu Thr Pro Pro Asp Gln Glu Val Ile Arg Asn Ile Asp Gln Ser
        675                 680                 685

Glu Phe Glu Gly Phe Ser Phe Val Asn Ser Glu Phe Leu Lys Pro Glu
    690                 695                 700

Val Lys Ser
705
```

PRKC FUSIONS

This application is a Division of U.S. application Ser. No. 15/326,359, filed Jan. 17, 2017, which is a National Stage Application of and claims priority under 35 USC § 371 to International Application No.: PCT/US2015/040560, filed Jul, 15, 2015, which claims the benefit of U.S. Provisional Application No. 62/025,865, filed Jul. 17, 2015, the contents of all of which are incorporated herein by reference in their entirety to provide continuity of disclosure.

The instant application contains a Sequence Listing which has been submitted electronically in ASCII format and is hereby incorporated by reference in its entirety. Said ASCII copy, created on Sep. 17, 2015, is named 12386.0009-00304_SL.txt and is 44,0322 bytes in size.

This invention relates to PRKC (protein kinase C family) gene fusions and PRKC fusion proteins. The invention further relates to methods of diagnosing and treating diseases or disorders associated with PRKC fusions, such as conditions mediated by aberrant PRKC expression or activity, or conditions associated with overexpression of PRKC.

Many forms of cancer are caused by genetic lesions that give rise to tumor initiation and growth. Genetic lesions may include chromosomal aberrations, such as translocations, inversions, deletions, copy number changes, gene expression level changes, and somatic and germline mutations. Indeed, the presence of such genomic aberrations is a hallmark feature of many cancers, including, for example, B cell cancer, lung cancer, breast cancer, ovarian cancer, pancreatic cancer, and colon cancer. In some models, cancer represents the phenotypic end-point of multiple genetic lesions that endow cells with a full range of biological properties required for tumorigenesis.

Recent efforts by The Cancer Genome Atlas (TCGA), the International Cancer Genome Consortium (ICGC), and dozens of other large-scale profiling efforts have generated an enormous amount of new sequencing data for dozens of cancer types—this includes whole-genome DNA, whole-exome DNA, and full-transcriptome RNA sequencing. These efforts have led to the identification of new driver genes and fusion genes within multiple cancer types. Fusions, particularly fusions involving kinases, are of particular interest, as such fusions have been shown to be oncogenic, and have been successfully targeted by new therapeutics. For example, anaplastic lymphoma kinase (ALK), one of the receptor tyrosine kinases, is known to become oncogenic when fused with various genes. See, e.g., M. Soda et al, "Identification of the transforming EML4-ALK fusion gene in non-small-cell lung cancer," *Nature* 444:561-566 (2007).

A need exists for identifying novel genetic lesions associated with cancer. For example, the presence of fusions involving a kinase in samples collected from more than one source can indicate that the kinase is an oncogenic driver. The identification of such fusions can be an effective approach to diagnosis of cancers and development of compounds, compositions, methods, and assays for evaluating and treating cancer patients.

In one aspect, the invention provides a method for detecting the presence of a PRKC fusion in a biological sample. The method includes the steps of: (a) obtaining a biological sample from a mammal; and (b) contacting the sample with a reagent that detects a PRKC fusion, to determine whether a PRKC fusion is present in the biological sample. The sample can be from, e.g., a cancer patient. In some embodiments, the cancer can be a lung cancer, such as, e.g., lung squamous cell carcinoma or lung adenocarcinoma. In some embodiments, the fusion can be, e.g., an IGF2BP3:PRKCA fusion, a TANC2:PRKCA fusion, an ADCY9:PRKCB fusion, or an SPNS1:PRKCB fusion. In some embodiments, the IGF2BP3:PRKCA fusion has all or part of the nucleotide and/or amino acid sequence (such as, e.g., the fusion junction) set forth in SEQ ID NO: 1 and SEQ ID NO:2, respectively. In some embodiments, the TANC2:PRKCA fusion has all or part of the nucleotide and/or amino acid sequence (such as, e.g., the fusion junction) set forth in SEQ ID NO:3 and SEQ ID NO:4, respectively. In some embodiments, the ADCY9:PRKCB fusion has all or part of the nucleotide and/or amino acid sequence (such as, e.g., the fusion junction) set forth in SEQ ID NO:5 and SEQ ID NO:6, respectively. In some embodiments, the SPNS1:PRKCB fusion has all or part of the nucleotide and/or amino acid sequence (such as, e.g., the fusion junction) set forth in SEQ ID NO:7 and SEQ ID NO:8, respectively.

In another aspect, the invention provides a method of diagnosing a patient having a disease or disorder associated with aberrant PRKC expression or activity, or overexpression of PRKC; the method includes: (a) obtaining a biological sample from the patient; and (b) contacting the sample with a reagent that detects a PRKC fusion to determine whether a PRKC fusion is present in the biological sample, whereby the detection of the PRKC fusion indicates the presence of a disorder associated with aberrant (e.g., constitutive) PRKC activity or expression, or overexpression of PRKC.

The invention also includes a method of determining a therapeutic regimen for treating a cancer in a human subject; a method of identifying a patient likely to respond to treatment with a PRKC inhibitor or a PRKC fusion inhibitor; a method of stratifying a patient population by detecting a PRKC fusion; a method of treating a patient; a method of inhibiting the proliferation of cells containing a PRKC fusion; a method of reducing an activity of a PRKC fusion; a method of treating a condition mediated by aberrant (e.g., constitutive) PRKC activity or expression; a method of treating a condition characterized by overexpression of PRKC; a method of identifying an agent that modulates the activity of a PRKC fusion; and a method of monitoring disease burden in a patient having a condition mediated by PRKC.

BRIEF DESCRIPTION OF THE FIGURES

FIG. 1 depicts the nucleotide sequence of an IGF2BP3:PRKCA gene fusion (SEQ ID NO: 1) comprising a portion of the IGF2BP3 gene (NM_006547) up to and including exon 10 and a portion of the PRKCA gene (NM_002737) starting at exon 4. The underlined codons at nucleotides 1201-1203 and 1204-1206 encode the last amino acid of IGF2BP3 and the first amino acid of PRKCA, respectively. The slash after nucleotide 1203 indicates the breakpoint (fusion junction) where translocation and in-frame fusion has occurred.

FIG. 2 depicts the amino acid sequence of an IGF2BP3:PRKCA fusion protein (SEQ ID NO:2). The slash between amino acids 401 and 402 indicates the breakpoint or fusion junction between the IGF2BP3 and PRKCA proteins. Amino acids 401-402 correspond to the codons at nucleotides 1201-1203 and 1204-1206 in SEQ ID NO:1.

FIG. 3 depicts the nucleotide sequence of a TANC2:PRKCA gene fusion (SEQ ID NO:3) comprising a portion of the TANC2 gene (NM 025185) up to and including exon 2 and a portion of the PRKCA gene (NM_002737) starting at exon 6. The underlined codons at nucleotides 136-138 and 142-144 encode the last amino acid of TANC2 and the first amino acid of PRKCA, respectively. The slash after nucleotide 139 indicates the breakpoint (fusion junction) where translocation and in-frame fusion has occurred. The shading at nucleotides 139-141 indicates that nucleotides from both TANC2 and PRKCA are fused in frame to form a codon and encode an amino acid.

FIG. 4 depicts the amino acid sequence of a TANC2: PRKCA fusion protein (SEQ ID NO:4). The shaded amino acid at position 47 corresponds to nucleotides 139-141 in SEQ ID NO:3. This amino acid is encoded by nucleotides from both TANC2 and PRKCA.

FIGS. 5A & 5B depict the nucleotide sequence of an ADCY9:PRKCB gene fusion (SEQ ID NO:5) comprising a ADCY9 gene (NM_001116) up to and including exon 2 and a portion of the PRKCB gene (NM_002738) starting at exon 3. The underlined codons at nucleotides 1690-1692 and 1696-1698 encode the last amino acid of ADCY9 and the first amino acid of PRKCB, respectively. The slash after nucleotide 1693 indicates the breakpoint (fusion junction) where translocation and in-frame fusion has occurred. The shading at nucleotides 1693-1695 indicates that nucleotides from both ADCY9 and PRKCB are fused in frame to form a codon and encode an amino acid.

FIG. 6 depicts the amino acid sequence of an ADCY9: PRKCB fusion protein (SEQ ID NO:6). The shaded amino acid at position 565 corresponds to the codon at nucleotides 1693-1695 in SEQ ID NO:5. This amino acid is encoded by nucleotides from both ADCY9 and PRKCB.

FIG. 7 depicts the nucleotide sequence of a SPNS1: PRKCB gene fusion (SEQ ID NO:7) comprising a SPNS1 gene (NM_001142451) up to and including exon 2 and a portion of the PRKCB gene (NM_002738) starting at exon 3. The underlined codons at nucleotides 304-306 and 310-312 encode the last amino acid of SPNS1 and the first amino acid of PRKCB, respectively. The slash after nucleotide 307 indicates the breakpoint (fusion junction) where translocation and in-frame fusion has occurred. The shading at nucleotides 307-309 indicates that nucleotides from both SPNS1 and PRKCB are fused in frame to form a codon and encode an amino acid.

FIG. 8 depicts the amino acid sequence of an SPNS1: PRKCB fusion protein (SEQ ID NO:8). The shaded amino acid at position 103 corresponds to the codon at nucleotides 307-309 in SEQ ID NO:7. This amino acid is encoded by nucleotides from both SPNS1 and PRKCA.

EXEMPLARY EMBODIMENTS OF THE INVENTION

The invention is based, at least in part, on the discovery of novel recombination or translocation events in cancer patients that result in at least a fragment of a PRKC gene linked to a non-homologous promoter via a recombination or translocation event that may result in aberrant expression (e.g., in a location where the kinase is not typically expressed) or overexpression of the kinase domain of the PRKC gene and thus, an increase in kinase activity. In some embodiments, the recombination or translocation may result in constitutive activation of PRKC kinase activity. Thus, a new patient population is identified, which is characterized by the presence of a PRKC fusion, e.g., a PRKC gene fusion or fusion protein. This new patient population suffers from or is susceptible to disorders mediated by aberrant (e.g., constitutive) PRKC activity or expression, or overexpression of PRKC, such as, e.g., a cancer. In another aspect of the invention, a new subtype of cancer is identified, which is characterized by the presence of the PRKC fusions described herein. In some embodiments, the new patient population suffers from or is susceptible to a lung cancer (such as, e.g., lung squamous cell carcinoma or lung adenocarcinoma) characterized by the presence of a PKRC fusion. New methods of diagnosing and treating the patient population and the PRKC fusion cancer subtype are also provided.

The term "PRKC fusion" is used generically herein, and includes any fusion molecule (e.g., gene, gene product (e.g., cDNA, mRNA, or protein), and variants thereof) that includes a fragment of PRKC, particularly the coding region for the kinase domain of PRKC, and a fragment of a second, non-homologous gene, such that the coding sequence for the kinase domain of PRKC is under control of the promoter of the non-homologous gene. In some embodiments, the PRKC fusion removes all or a portion of the coding region of the regulatory domain of PRKC, such as, e.g., the autoinhibitory pseudosubstrate segment. A PRKC fusion protein generally includes the kinase domain of PRKC.

PRKC Gene Fusions and Fusion Proteins

PRKC is a family of protein kinase enzymes that are involved in controlling the function of other proteins through the phosphorylation of hydroxyl groups of serine and threonine amino acid residues on these proteins. PRKC in turn is activated by signals such as increases in the cellular concentration of diacylglycerol (DAG) or calcium ions ($Ca^{2+}$) and plays important roles in several signal transduction cascades. The activity of PRKC itself is also regulated by phosphorylation. The PRKC family contains fifteen isozymes in humans, which are divided into three subfamilies based on their second messenger requirements: conventional (or classical), novel, and atypical. Isoforms a (protein kinase C, alpha (PRKCA)) and $\beta_I$ and $\beta_{II}$ (protein kinase C, beta (PRKCB)) belong to the conventional subfamily. The structure of PRKC contains a regulatory domain and a catalytic domain tethered together by a hinge region. The regulatory domain at the N-terminus of PRKC includes the pseudosubstrate segment, which is a small sequence of amino acids that mimic a substrate and bind the substrate-binding cavity in the catalytic domain, keeping the enzyme inactive. When $Ca^{2+}$ and DAG are present in sufficient concentrations, they bind to the regulatory domain and recruit PRKC to the membrane. This interaction with the membrane results in release of the pseudosubstrate segment from the catalytic site and activation of the enzyme. The catalytic region includes the kinase domain of PRKC. Upon activation, PRKC is translocated to the plasma membrane and carries out PRKC-mediated phosphorylation of substrate proteins. PRKC fusions have recently been described in papillary glioneuronal tumors (see Bridge, J. A. et al, *Brain Pathol. Zurich Switz.* 23: 121-128 (2013)) and benign fibrous histiocytoma (see Plaszczyca, A. et al, *Int. J. Biochem. Cell Biol.* doi:10.1016/j.biocel.2014.03.027 (2014)).

The invention provides novel PRKC fusions that are associated with different types of disorders. For example, the PRKC fusions disclosed herein can be associated with certain cancers, such as, e.g., a lung cancer. In some embodiments, the lung cancer associated with a PRKC fusion is lung squamous carcinoma or lung adenocarcinoma. In some embodiments, the PRKC fusions disclosed herein can be associated with other disorders mediated by aberrant (e.g., constitutive) PRKC activity or expression, or overexpression of PRKC.

PRKC gene fusions are generated by a fusion between at least a part of the PRKC gene, such as, e.g., PRKCA or PRKCB, and a part of another gene as a result of a translocation (including inversion) within a chromosome or between chromosomes. As a result of a translocation, the PRKC gene may be placed under the transcriptional control of the partner gene promoter, resulting in aberrant PRKC activity or expression or overexpression of PRKC. Alternatively or additionally, the translocation may result in removal of all or a portion of the regulatory domain of PRKC, such as, e.g., the autoinhibitory pseudosubstrate segment, and cause PRKC to become constitutively activated. The overexpression and/or constitutive activation can lead to certain cancers. As used herein, the 5'-region is upstream of, and the 3'-region is downstream of, a fusion junction or breakpoint in one of the component genes. PRKC and the gene or protein that it is fused to is referred to as "fusion partners." Alternatively, they may be identified as a "PRKC gene fusion" or a "PRKC fusion protein," which are collectively termed "PRKC fusions." The PRKC fusions disclosed herein have a kinase activity. The phrase "having a kinase activity" as used in this application means having an activity as an enzyme phosphorylating the side chain of an amino acid, such as serine or threonine. In some embodiments, the PRKC fusion may include an in-frame fusion of the coding sequences of PRKC and the fusion partner that introduces amino acids into the fusion protein that are not part of PRKC or the fusion partner.

In some exemplary embodiments, the fusion partner is all or a portion of IGF2BP3 (insulin-like growth factor 2 mRNA binding protein 3). In other exemplary embodiments, the fusion partner is all or a portion of TANC2 (tetratricopeptide repeat, ankyrin repeat and coiled-coil containing 2). In other exemplary embodiments, the fusion partner is all or a portion of ADCY9 (adenylate cyclase type 9). In yet other exemplary embodiments, the fusion partner is all or a portion of SPNS1 (spinster homolog 1). In some embodiments, the PRKC gene is PRKCA. In other embodiments, the PRKC gene is PRKCB.

Reference to "all or a portion" or "all or part" of a PRKC gene fusion or SEQ ID NO: 1, 3, 5, or 7, means that the nucleotide sequence comprises the entire PRKC gene fusion nucleotide sequence or a fragment of that sequence that comprises the fusion junction or breakpoint between PRKC and its fusion partner (such as, e.g., IGF2BP3, TANC2, ADCY9, or SPNS1). The fragment may comprise 7, 8, 9, 10, 12, 14, 16, 18, 20, 21, 22, 23, 24, 25, 26, 27, 28, 29, 30, 35, 40, 45, 50, 60, 70, 80, 90, 100, 120, 150, 175, 200, 250, 300, or more nucleotides spanning the fusion junction of the PRKC gene fusion. Reference to "all or a portion" or "all or part" of a PRKC fusion protein or SEQ ID NO:2, 4, 6, or 8, means an amino acid sequence that comprises the entire PRKC fusion protein amino acid sequence or a fragment of that sequence that comprises the fusion junction or breakpoint between PRKC and its fusion partner (such as, e.g., IGF2BP3, TANC2, ADCY9, or SPNS1). The fragment may comprise 8, 10, 12, 14, 15, 16, 18, 20, 21, 22, 23, 24, 25, 26, 27, 28, 29, 30, 35, 40, 45, 50, 75, or more amino acids spanning the fusion junction.

In certain embodiments of the invention, a fusion includes an in-frame fusion of all or a portion of the IGF2BP3 gene (e.g., an IGF2BP3 promotor or a functional fragment thereof, and one or more exons encoding IGF2BP3 or a fragment thereof) and an exon of the PRKCA gene (e.g., one or more exons encoding a PRKCA kinase domain or a functional fragment thereof). Such a fusion can be referred to as an IGF2BP3:PRKCA fusion. In one embodiment, the IGF2BP3:PRKCA fusion comprises sufficient PRKCA sequence to drive expression of a fusion protein that has kinase activity, e.g., has elevated activity as compared with wild type PRKCA in the same tissue or cell. In some embodiments, the IGF2BP3:PRKCA fusion removes all or a portion of the sequence encoding the regulatory domain of PRKCA, such as, e.g., the autoinhibitory pseudosubstrate segment, and results in expression of a fusion protein that has constitutive kinase activity, e.g., has activity without upstream signaling or binding of a ligand or second messenger, such as, e.g., DAG or $Ca^{2+}$.

In some embodiments, the invention provides an IGF2BP3:PRKC gene fusion comprising the nucleotide sequence depicted in FIG. 1 (SEQ ID NO: 1), or a fragment thereof that includes the fusion junction. SEQ ID NO:1 comprises IGF2BP3 (NM_006547) up to exon 10 fused to PRKCA (NM_002737), beginning at exon 4. In some embodiments, the IGF2BP3:PRKCA gene fusion comprises a nucleotide sequence that is at least 85%, at least 90%, at least 95%, at least 97%, at least 98%, or at least 99% identical to all or part of SEQ ID NO:1. In some embodiments, the IGF2BP3:PRKCA gene fusion encodes a protein having the sequence depicted in FIG. 2 (SEQ ID NO:2) or a sequence that is at least 85%, at least 90%, at least 95%, at least 97%, at least 98%, or at least 99% identical to all or part of SEQ ID NO:2.

In other embodiments of the invention, a fusion includes an in-frame fusion of all or a portion of the TANC2 gene (e.g., a TANC2 promotor or a functional fragment thereof, and one or more exons encoding a TANC2 or a fragment thereof) and an exon of the PRKCA gene (e.g., one or more exons encoding a PRKCA kinase domain or a functional fragment thereof). Such a fusion can be referred to as a TANC2:PRKCA fusion. In one embodiment, the TANC2:PRKCA fusion comprises sufficient PRKCA sequence to drive expression of a fusion protein that has kinase activity, e.g., has elevated activity as compared with wild type PRKCA in the same tissue or cell. In some embodiments, the TANC2:PRKCA fusion removes all or a portion of the sequence encoding the regulatory domain of PRKCA, such as, e.g., the autoinhibitory pseudosubstrate segment, and results in expression of a fusion protein that has constitutive kinase activity, e.g., has activity without upstream signaling or binding of a ligand or second messenger, such as, e.g., DAG or $Ca^{2+}$.

In some embodiments, the invention provides an TANC2:PRKCA gene fusion comprising the nucleotide sequence depicted in FIG. 3 (SEQ ID NO:3), or a fragment thereof that includes the fusion junction. SEQ ID NO:3 comprises TANC2 (NM_025185) up to exon 2 fused to PRKCA (NM_002737), beginning at exon 6. In some embodiments, the TANC2:PRKCA gene fusion comprises a nucleotide sequence that is at least 85%, at least 90%, at least 95%, at least 97%, at least 98%, or at least 99% identical to all or part of SEQ ID NO:3. In some embodiments, the TANC2:PRKCA gene fusion encodes a protein having the sequence depicted in FIG. 4 (SEQ ID NO:4) or a sequence that is at least 85%, at least 90%, at least 95%, at least 97%, at least 98%, or at least 99% identical to all or part of SEQ ID NO:4.

In certain embodiments of the invention, a fusion includes an in-frame fusion of all or a portion of the ADCY9 gene (e.g., an ADCY9 promotor or a functional fragment thereof, and one or more exons encoding an ADCY9 or a fragment thereof) and an exon of the PRKCB gene (e.g., one or more exons encoding a PRKCB kinase domain or a functional fragment thereof). Such a fusion can be referred to as an ADCY9:PRKCB fusion. In some embodiments, the ADCY9:PRKCB fusion comprises sufficient PRKCB sequence to drive expression of a fusion protein that has kinase activity, e.g., has elevated activity as compared with wild type PRKCB in the same tissue or cell. In some embodiments, the ADCY9:PRKCB fusion removes all or a portion of the sequence encoding the regulatory domain of PRKCB, such as, e.g., the autoinhibitory pseudosubstrate segment, and results in expression of a fusion protein that has constitutive kinase activity, e.g., has activity without upstream signaling or binding of a ligand or second messenger, such as, e.g., DAG or $Ca^{2+}$.

In some embodiments, the ADCY9:PRKCB fusion has the nucleotide sequence depicted in FIG. 5 (SEQ ID NO:5), or a fragment thereof that includes the fusion junction. SEQ ID NO:5 comprises ADCY9 (NM_001116) up to and including exon 2 fused to PRKCB (NM_002738), beginning at exon 3. In some embodiments, the ADCY9:PRKCB gene fusion comprises a nucleotide sequence that is at least 85%, at least 90%, at least 95%, at least 97%, at least 98%, or at least 99% identical to all or part of SEQ ID NO:5. In some embodiments, the ADCY9:PRKCB fusion encodes a protein having the sequence depicted in FIG. 6 (SEQ ID NO:6) or a sequence that is at least 85%, at least 90%, at least 95%, at least 97%, at least 98%, or at least 99% identical to all or part of SEQ ID NO:6.

In certain embodiments of the invention, a fusion includes an in-frame fusion of all or a portion of the SPNS1 gene (e.g., an SPNS1 promotor or a functional fragment thereof, and one or more exons encoding an SPNS1 or a fragment thereof) and an exon of the PRKCB gene (e.g., one or more exons encoding a PRKCB kinase domain or a functional fragment thereof). Such a fusion can be referred to as an SPNS1:PRKCB fusion. In one embodiment, the SPNS1:PRKCB fusion comprises sufficient PRKCB sequence to drive expression of a fusion protein that has kinase activity, e.g., has elevated activity as compared with wild type PRKCB in the same tissue or cell. In some embodiments, the SPNS1:PRKCB fusion removes all or a portion of the sequence encoding the regulatory domain of PRKCB, such as, e.g., the autoinhibitory pseudosubstrate segment, and results in expression of a fusion protein that has constitutive kinase activity, e.g., has activity without upstream signaling or binding of a ligand or second messenger, such as, e.g., DAG or $Ca^{2+}$.

In some embodiments, the invention provides an SPNS1:PRKCB3 gene fusion comprising the nucleotide sequence depicted in FIG. 7 (SEQ ID NO:7), or a fragment of thereof that includes the fusion junction. SEQ ID NO:7 comprises SPNS1 (NM_001142451) up to exon 2 fused to PRKCB (NM_002738), beginning at exon 3. In some embodiments, the SPNS1:PRKCB gene fusion comprises a nucleotide sequence that is at least 85%, at least 90%, at least 95%, at least 97%, at least 98%, or at least 99% identical to all or part of SEQ ID NO:7. In some embodiments, the SPNS1:PRKCB gene fusion encodes a protein having the sequence depicted in FIG. 8 (SEQ ID NO:8) or a sequence that is at least 85%, at least 90%, at least 95%, at least 97%, at least 98%, or at least 99% identical to all or part of SEQ ID NO:8.

The nucleic acid sequences of PRKC gene fusions may be used as probes, primers, or bait to identify nucleotides from a biological sample that include, flank, or hybridize to, PRKC fusions, such as IGF2BP3:PRKCA (e.g., all or part of SEQ ID NO: 1), TANC2:PRKCA (e.g., all or part of SEQ ID NO:3), ADCY9:PRKCB (e.g., all or part of SEQ ID NO:5), or SPNS1:PRKCB (e.g., all or part of SEQ ID NO:7), at, e.g., the fusion junctions. In certain embodiments, the probe, primer, or bait molecule is an oligonucleotide that allows capture, detection, and/or isolation of a PRKC gene fusion in a biological sample. In certain embodiments, the probes or primers derived from the nucleic acid sequences of PRKC gene fusions (e.g., from the fusion junctions) may be used, for example, for polymerase chain reaction (PCR) amplification. The oligonucleotide can comprise a nucleotide sequence substantially complementary to a fragment of the PRKC gene fusion nucleic acid molecules described herein. The sequence identity between the nucleic acid fragment, e.g., the oligonucleotide and the target PRKC gene fusion sequence, need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length that includes the fusion junction of a PRKC fusion, such as, e.g., IGF2BP3:PRKCA (e.g., all or part of SEQ ID NO: 1), TANC2:PRKCA (e.g., all or part of SEQ ID NO:3), ADCY9:PRKCB (e.g., all or part of SEQ ID NO:5), or SPNS1:PRKCB (e.g., all or part of SEQ ID NO:7). In other embodiments, the nucleic acid fragment is a bait that includes an oligonucleotide between about 100 to 300 nucleotides, 130 and 230 nucleotides, or 150 and 200 nucleotides in length that includes the fusion junction of a PRKC fusion, such as, e.g., IGF2BP3:PRKCA (e.g., all or part of SEQ ID NO: 1), TANC2:PRKCA (e.g., all or part of SEQ ID NO: 3), ADCY9:PRKCB (e.g., all or part of SEQ ID NO:5), or SPNS1:PRKCB (e.g., all or part of SEQ ID NO:7).

In certain embodiments, the nucleic acid fragments hybridize to a nucleotide sequence that includes a breakpoint or fusion junction, e.g., a breakpoint or fusion junction as identified by a slash ("/") in FIGS. 1, 3, 5, or 7. For example, the nucleic acid fragment can hybridize to a nucleotide sequence that includes the fusion junction between the IGF2BP3 transcript and the PRKCA transcript (e.g., nucleotides 1201-1206 of SEQ ID NO: 1), between the TANC2 transcript and the PRKCA transcript (e.g., nucleotides 136-144 of SEQ ID NO:3), between the ADCY9 transcript and the PRKCB transcript (e.g., nucleotides 1690-1698 of SEQ ID NO:5), or between the SPNS1 transcript and the PRKCB transcript (e.g., nucleotides 304-312 of SEQ ID NO:7), i.e., a nucleotide sequence that includes a portion of SEQ ID NO: 1, 3, 5, or 7.

In other embodiments, the nucleic acid fragment includes a bait that comprises a nucleotide sequence that hybridizes to a PRKC gene fusion nucleic acid molecule described herein, and thereby allows the detection, capture, and/or isolation of the nucleic acid molecule. In one embodiment, a bait is suitable for solution phase hybridization. In other embodiments, a bait includes a binding entity or detection entity, e.g., an affinity tag or fluorescent label, that allows detection, capture, and/or separation, e.g., by binding to a binding entity, of a hybrid formed by a bait and a nucleic acid hybridized to the bait.

In exemplary embodiments, the nucleic acid fragments hybridize to a nucleotide sequence that includes a fusion junction between the IGF2BP3 transcript and the PRKCA transcript, e.g., a nucleotide sequence within SEQ ID NO: 1 comprising nucleotides 1201-1206 (such as, e.g., a sequence comprising nucleotides 1199-1208, 1194-1213, 1179-1228, or 1154-1253 of SEQ ID NO:1).

In other exemplary embodiments, the nucleic acid fragments hybridize to a nucleotide sequence that includes a fusion junction between the TANC2 transcript and the PRKCA transcript, e.g., a nucleotide sequence within SEQ ID NO:3 comprising nucleotides 136-144 (such as, e.g., a sequence comprising nucleotides 134-146, 129-151, 114-166, or 89-191 of SEQ ID NO:3).

In other exemplary embodiments, the nucleic acid fragments hybridize to a nucleotide sequence that includes a fusion junction between the ADCY9 transcript and the PRKCB transcript, e.g., a nucleotide sequence within SEQ ID NO:5 comprising nucleotides 1690-1698 (such as, e.g., a sequence comprising nucleotides 1688-1700, 1683-1705, 1668-1720, or 1643-1745 of SEQ ID NO:5).

In other exemplary embodiments, the nucleic acid fragments hybridize to a nucleotide sequences that includes a fusion junction between the SPNS1 transcript and the PRKCB transcript, e.g., a nucleotide sequence within SEQ ID NO:7 comprising nucleotides 304-312 (such as, e.g., a sequence comprising nucleotides 302-314, 297-319, 282-334, or 257-359 of SEQ ID NO:7).

Another aspect of the invention provides PRKC fusion proteins (such as, e.g., a purified or isolated IGF2BP3:PRKCA, TANC2:PRKCA, ADCY9:PRKCB, or SPNS1:PRKCB fusion protein), biologically active or antigenic fragments thereof, and use of those polypeptides for detecting and/or modulating the biological activity (such as tumorigenic activity) of a PRKC fusion protein. Exemplary embodiments of the PRKC fusion proteins comprise the amino acid sequence set forth in SEQ ID NO:2, 4, 6, or 8, and fragments of those sequences.

In some embodiments, the PRKC fusion protein of the invention can include a fragment of an IGF2BP3 protein, a TANC2 protein, an ADCY9 protein, or an SPNS1 protein, and a fragment of a PRKC protein, such as, e.g., a PRKCA protein or a PRKCB protein. In one embodiment, the PRKC fusion protein is an IGF2BP3:PRKCA fusion protein having the amino acid sequence of SEQ ID NO:2 or a fragment thereof, such as, e.g., amino acids 397-406, 392-411, or 377-426 of SEQ ID NO:2. In other embodiments, the PRKC fusion protein is a TANC2:PRKCA fusion protein having the amino acid sequence of SEQ ID NO:4 or a fragment thereof, such as, e.g., amino acids 42-51, 37-56, or 22-71 of SEQ ID NO:4. In some embodiments, the PRKC fusion protein is an ADCY9:PRKCB fusion protein having the amino acid sequence of SEQ ID NO:6 or a fragment thereof, such as, e.g., amino acids 560-569, 555-574, or 540-589 of SEQ ID NO:6. In other embodiments, the PRKC fusion protein is an SPNS1:PRKCB fusion protein having the amino acid sequence of SEQ ID NO:8, or a fragment thereof, such as, e.g., amino acids 98-107, 93-112, or 78-127 of SEQ ID NO:8.

In some embodiments, the PRKC fusion protein is an IGF2BP3:PRKCA fusion protein comprising an amino acid sequence that is at least 85%, at least 90%, at least 95%, at least 97%, at least 98%, or at least 99% identical to SEQ ID NO:2 or a fragment thereof (e.g., amino acids 397-406, 392-411, or 377-426 of SEQ ID NO:2). In other embodiments, the PRKC fusion protein is a TANC2:PRKCA fusion protein comprising an amino acid sequence that is at least 85%, at least 90%, at least 95%, at least 97%, at least 98%, or at least 99% identical to SEQ ID NO:4 or a fragment thereof (e.g., amino acids 42-51, 37-56, or 22-71 of SEQ ID NO:4). In yet other embodiments, the PRKC fusion protein is an ADCY9:PRKCB fusion protein comprising an amino acid sequence that is at least 85%, at least 90%, at least 95%, at least 97%, at least 98%, or at least 99% identical to SEQ ID NO:6 or a fragment thereof (e.g., amino acids 560-569, 555-574, or 540-589 of SEQ ID NO:6). In some embodiments the PRKC fusion protein is an SPNS1:PRKCB fusion protein comprising an amino acid sequence that is at least 85%, at least 90%, at least 95%, at least 97%, at least 98%, or at least 99% identical to SEQ ID NO:8 or a fragment thereof (e.g., amino acids 98-107, 93-112, or 78-127 of SEQ ID NO:8).

In certain embodiments, the PRKC fusion protein includes a functional kinase domain. In some embodiments, the PRKC fusion protein comprises elevated PRKC activity as compared with wild type PRKC activity (e.g., in a cancer cell, a non-cancer cell adjacent to the cancer cell, or a non-cancer cell from a control sample, such as a cancer free subject). In some embodiments, the PRKC fusion protein removes all or a portion of the regulatory domain of PRKC, such as, e.g., the autoinhibitory pseudosubstrate segment. In such embodiments, the PRKC fusion protein comprises constitutive kinase activity, e.g., has activity without upstream signaling or binding of a ligand or second messenger, such as, e.g., DAG or $Ca^{2+}$. In one exemplary embodiment, the PRKC fusion protein is an IGF2BP3:PRKCA fusion and includes a PRKC serine/threonine kinase domain or a functional fragment thereof. In other exemplary embodiments, the PRKC fusion protein is a TANC2:PRKCA fusion and includes a PRKC serine/threonine kinase domain or a functional fragment thereof. In some exemplary embodiments, the PRKC fusion protein is an ADCY9:PRKCB fusion and includes a PRKC serine/threonine kinase domain or a functional fragment thereof. In yet other exemplary embodiments, the PRKC fusion protein is an SPNS1:PRKCB fusion and includes a PRKC serine/threonine kinase domain or a functional fragment thereof.

In another embodiment, the PRKC fusion protein or fragment is a peptide, e.g., an immunogenic peptide or protein, that contains a fusion junction with a heterologous protein as described herein. Such immunogenic peptides or proteins can be used for vaccine preparation for use in the treatment or prevention of cancers caused by or exacerbated by PRKC gene fusions and PRKC fusion proteins. In other embodiments, such immunogenic peptides or proteins can be used to raise antibodies specific to the fusion protein. In some embodiments, the PRKC fusion protein is present in combination with or is further conjugated to one or more adjuvant(s) or immunogen(s), e.g., a protein capable of enhancing an immune response to the PRKC fusion protein (e.g., a hapten, a toxoid, etc.). In some embodiments, the PRKC fusion protein is an IGF2BP3:PRKCA, TANC2:PRKCA, ADCY9:PRKCB, or SPNS1:PRKCB fusion protein. In some embodiments, the PRKC fusion protein comprises the fusion junction of SEQ ID NO:2, 4, 6, or 8.

Thus, another aspect of the invention provides an antibody that binds to a PRKC fusion protein (such as, e.g., an IGF2BP3:PRKCA, a TANC2:PRKCA, an ADCY9:PRKCB, or an SPNS1:PRKCB fusion protein) or a fragment thereof. In certain embodiments, the antibody recognizes a PRKC fusion protein but does not recognize wild type PRKC or the wild type fusion partner (such as, e.g., IGF2BP3, TANC2, ADCY9, or SPNS1). In some embodiments, the antibody binds to an epitope comprising the junction between PRKC and the fusion partner (e.g., the junction of IGF2BP3:PRKCA, TANC2:PRKCA, ADCY9:PRKCB, or SPNS1:PRKCB). In one embodiment, the antibody binds to an IGF2BP3:PRKCA fusion protein having the amino acid sequence of SEQ ID NO:2 or a fragment thereof, such as, e.g., amino acids 397-406, 392-411, or 377-426 of SEQ ID NO:2. In other embodiments, the antibody binds to a TANC2:PRKCA fusion protein having the amino acid sequence of SEQ ID NO:4 or a fragment thereof, such as, e.g., amino acids 42-51, 37-56, or 22-71 of SEQ ID NO:4. In some embodiments, the antibody binds to an ADCY9:PRKCB fusion protein having the amino acid sequence of SEQ ID NO:6 or a fragment thereof, such as, e.g., amino acids 560-569, 555-574, or 540-589 of SEQ ID NO:6. In other embodiments, the antibody binds to an SPNS1: PRKCB fusion protein having the amino acid sequence of SEQ ID NO:8 or a fragment thereof, such as, e.g., amino acids 98-107, 93-112, or 78-127 of SEQ ID NO:8.

In certain embodiments, the antibodies of the invention inhibit and/or neutralize the biological activity of the PRKC fusion protein, and more specifically, in some embodiments, the kinase activity of the PRKC fusion protein. In other embodiments, the antibodies may be used to detect a PRKC fusion protein or to diagnose a patient suffering from a disease or disorder associated with the expression of a PRKC fusion protein.

Detection and Diagnostic Methods

In another aspect, the invention provides a method of detecting the presence of a PRKC gene fusion or fusion protein, such as, e.g., an IGF2BP3:PRKCA, a TANC2: PRKCA, an ADCY9:PRKCB, or an SPNS1:PRKCB fusion as described herein. The presence of a PRKC fusion indicates that the mammal providing the biological sample suffers from or is at risk of developing a disorder mediated by aberrant (e.g., constitutive) PRKC activity or expression, or overexpression of PRKC, such as, e.g., a cancer. The presence of a PRKC fusion may also indicate that the disorder is treatable with a PRKC inhibitor, such as, e.g., a kinase inhibitor or an antibody specific to PRKC, or a PRKC fusion inhibitor. In some embodiments, the cancer is lung cancer. In some embodiments, the cancer is lung squamous cell carcinoma. In some embodiments, the cancer is lung adenocarcinoma. In some embodiments, the PRKC fusion present in the sample is IGF2BP3:PRKCA, TANC2: PRKCA, or ADCY9:PRKCB and the cancer to be treated is lung squamous cell carcinoma. In other embodiments, the PRKC fusion present in the sample is SPNS1:PRKCB and the cancer to be treated is lung adenocarcinoma.

In one embodiment, the PRKC fusion detected is a nucleic acid molecule or a polypeptide. The method includes detecting whether a PRKC fusion nucleic acid molecule or polypeptide is present in a cell (e.g., a circulating cell or a cancer cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

The sample can be chosen from one or more sample types, such as, for example, tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow.

I. Methods for Detecting Gene Fusions

In certain embodiments, the sample is acquired from a subject having or at risk of having a cancer (e.g., a patient), or alternatively, the method further includes acquiring a sample from the subject. In some embodiments, the PRKC fusion is detected in a nucleic acid molecule by a method chosen from one or more of: e.g., nucleic acid hybridization assay (e.g. in situ hybridization, comparative genomic hybridization, microarray, Southern blot, northern blot), amplification-based assays (e.g., PCR, PCR-RFLP assay, or real-time PCR), sequencing and genotyping (e.g. sequence-specific primers, high-performance liquid chromatography, or mass-spectrometric genotyping), and screening analysis (including metaphase cytogenetic analysis by karyotype methods.

(1) Hybridization Methods

In some embodiments, the reagent hybridizes to a PRKC gene fusion, such as, e.g., nucleotides 1201-1206, 1199-1208, 1194-1213, 1179-1228, or 1154-1253 of SEQ ID NO:1. In alternate embodiments, the reagent detects the presence of nucleotides 136-144, 134-146, 129-151, 114-166, or 89-191 of SEQ ID NO:3, nucleotides 1690-1698, 1688-1700, 1683-1705, 1668-1720, or 1643-1745 of SEQ ID NO:5, or nucleotides 304-312, 302-314, 297-319, 282-334, or 257-359 of SEQ ID NO:7. In one embodiment, the method includes: contacting a nucleic acid sample, e.g., a genomic DNA sample (e.g., a chromosomal sample or a fractionated, enriched or otherwise pre-treated sample) or a gene product (e.g., mRNA, or cDNA), obtained from the subject, with a nucleic acid fragment e.g., a probe or primer as described herein (e.g., an exon-specific or a breakpoint-specific probe or primer), under conditions suitable for hybridization, and determining the presence or absence of the PRKC gene fusion, such as, e.g. IGF2BP3:PRKCA, TANC2:PRKCA, ADCY9:PRKCB, or SPNS1:PRKCB. In an alternate embodiment, the method includes the steps of obtaining a sample; exposing the sample to a nucleic acid probe which hybridizes to an mRNA or cDNA encoding a PRKC fusion protein that comprises amino acids 397-406, 392-411, or 377-426 of SEQ ID NO:2, amino acids 42-51, 37-56, or 22-71 of SEQ ID NO:4, amino acids 560-569, 555-574, or 540-589 of SEQ ID NO:6, or amino acids 98-107, 93-112, or 78-127 of SEQ ID NO:8.

Hybridization, as described throughout the specification, may be carried out under stringent conditions, e.g., medium or high stringency. See, e.g., J. Sambrook, E. F. Fritsch, and T. Maniatis, *Molecular Cloning: A Laboratory Manual*, Cold Spring Harbor Laboratory Pr; 2nd edition (1989): T. Brown, *Hybridization Analysis of DNA Blots, Current Protocols in Molecular Biology* at 21:2.10.1-2.10.16 (2001). High stringency conditions for hybridization refer to conditions under which two nucleic acids must possess a high degree of base pair homology to each other in order to hybridize. Examples of highly stringent conditions for hybridization include hybridization in 4×sodium chloride/ sodium citrate (SSC), at 65 or 70° C., or hybridization in 4×SSC plus 50% formamide at about 42 or 50° C., followed by at least one, at least two, or at least three washes in 1SSC, at 65 or 70° C. Another example of highly stringent conditions includes hybridization in 2×SSC; 10×Denhardt solution (Fikoll 400+PEG+BSA; ratio 1:1:1); 0.1% SDS; 5 mM EDTA; 50 mM Na$_2$HPO$_4$; 250 µg/ml of herring sperm DNA; 50 µg/ml of tRNA; or 0.25 M of sodium phosphate buffer, pH 7.2; 1 mM EDTA7% SDS at 60° C.; followed by washing 2×SSC, 0.1% SDS at 60° C.

The nucleic acid fragments can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag, or identifier (e.g., an adaptor, barcode or other sequence identifier). Labeled or unlabeled nucleic acids and/or nucleic acid fragments may be used in reagents for detecting, capturing, or isolating PRKC gene fusions. Labeled or unlabeled nucleic acids and/or nucleic acid fragments may be used in reagents for detecting, capturing, and/or isolating PRKC gene fusions, such as, e.g., IGF2BP3: PRKCA (e.g., all or part of SEQ ID NO:1), TANC2:PRKCA (e.g., all or part of SEQ ID NO:3). ADCY9:PRKCB (e.g., all or part of SEQ ID NO:5), or SPNS1:PRKCB (e.g., all or part of SEQ ID NO:7). In some embodiments, the labeled reagent can be detected using, e.g., autoradiography, microscopy (e.g., brightfield, fluorescence, or electron microscopy), enzyme-linked immunosorbent assay (ELISA), or immunohistochemistry.

In some embodiments, the method comprises performing chromosome in situ hybridization with chromosomal DNA from a biological sample to detect the presence of a PRKC gene fusion (such as, e.g., IGF2BP3:PRKCA, TANC2:PRKCA, ADCY9:PRKCB, or SPNS1:PRKCB, as disclosed herein). In some embodiments, the chromosome in situ hybridization comprises the steps of: providing a chromosome (e.g., interphase or metaphase chromosome) preparation (e.g., by attaching the chromosomes to a substrate (e.g., glass)); denaturing the chromosomal DNA (e.g., by exposure to formamide) to separate the double strands of the polynucleotides from each other; exposing the nucleic acid probe to the chromosomes under conditions to allow hybridization of the probe to the target DNA; removing unhybridized or non-specifically hybridized probes by washing; and detecting the hybridization of the probe with the target DNA. In some embodiments, the chromosome in situ hybridization is fluorescence in situ hybridization (FISH). In some embodiments, the probe is labeled directly by a fluorescent label, or indirectly by incorporation of a nucleotide containing a tag or reporter molecule (e.g., biotin, digoxigenin, or hapten) which after hybridization to the target DNA is then bound by fluorescently labeled affinity molecule (e.g., an antibody or streptavidin). In some embodiments, the hybridization of the probe with the target DNA in FISH can be visualized using a fluorescence microscope.

In other embodiments, the method comprises performing Southern blot with DNA polynucleotides from a biological sample to detect the presence of a PRKC gene fusion (such as, e.g., IGF2BP3:PRKCA, TANC2:PRKCA, ADCY9:PRKCB, or SPNS1:PRKCB, as disclosed herein). In some embodiments, the Southern blot comprises the steps of: optionally fragmenting the polynucleotides into smaller sizes by restriction endonucleases; separating the polynucleotides by gel electrophoresis; denaturing the polynucleotides (e.g., by heat or alkali treatment) to separate the double strands of the polynucleotides from each other; transferring the polynucleotides from the gel to a membrane (e.g., a nylon or nitrocellulose membrane); immobilizing the polynucleotides to the membrane (e.g., by UV light or heat); exposing the nucleic acid probe to the polynucleotides under conditions to allow hybridization of the probe to the target DNA; removing unhybridized or non-specifically hybridized probes by washing; and detecting the hybridization of the probe with the target DNA.

(2) Amplification-Based Assays

In certain embodiments, the method of detecting the presence of a PRKC gene fusion, comprises (a) performing a PCR amplification reaction with polynucleotides from a biological sample, wherein the amplification reaction utilizes a pair of primers which will amplify at least a fragment of the PRKC gene fusion, wherein the fragment comprises the fusion junction, wherein the first primer is in sense orientation and the second primer is in antisense orientation; and (b) detecting an amplification product, wherein the presence of the amplification product is indicative of the presence of a PRKC fusion polynucleotide in the sample. In specific exemplary embodiments, the PRKC gene fusion is IGF2BP3:PRKCA, such as, e.g., the gene fusion of SEQ ID NO: 1 or a fragment thereof comprising nucleotides 1201-1206, 1199-1208, 1194-1213, 1179-1228, or 1154-1253 of SEQ ID NO:1 In other exemplary embodiments, the gene fusion is TANC2:PRKCA such as, e.g. the gene fusion of SEQ ID NO:3 or a fragment thereof comprising nucleotides 136-144, 134-146, 129-151, 114-166, or 89-191 of SEQ ID NO:3. In other exemplary embodiments, the gene fusion is ADCY9:PRKCB such as, e.g. the gene fusion of SEQ ID NO:5 or a fragment thereof comprising nucleotides 1690-1698, 1688-1700, 1683-1705, 1668-1720, or 1643-1745 of SEQ ID NO:5. In certain exemplary embodiments, the gene fusion is SPNS1:PRKCB such as, e.g. the gene fusion of SEQ ID NO:7 or a fragment thereof comprising nucleotides 304-312, 302-314, 297-319, 282-334, or 257-359 of SEQ ID NO:7.

In some embodiments, step (a) of performing a PCR amplification reaction comprises: (i) providing a reaction mixture comprising the polynucleotides (e.g., DNA or cDNA) from the biological sample, the pair of primers which will amplify at least a fragment of the PRKC gene fusion wherein the first primer is complementary to a sequence on the first strand of the polynucleotides and the second primer is complementary to a sequence on the second strand of the polynucleotides, a DNA polymerase, and a plurality of free nucleotides comprising adenine, thymine, cytosine, and guanine (dNTPs); (ii) heating the reaction mixture to a first predetermined temperature for a first predetermined time to separate the double strands of the polynucleotides from each other; (iii) cooling the reaction mixture to a second predetermined temperature for a second predetermined time under conditions to allow the first and second primers to hybridize with their complementary sequences on the first and second strands of the polynucleotides, and to allow the DNA polymerase to extend the primers; and (iv) repeating steps (ii) and (iii) for a predetermined number of cycles (e.g., 10, 15, 20, 25, 30, 35, 40, 45, or 50 cycles).

In some embodiments, the polynucleotides from the biological sample comprise RNA, and the method further comprises performing a RT-PCR amplification reaction with the RNA to synthesize cDNA as the template for subsequent or simultaneous PCR reactions. In some embodiments, the RT-PCR amplification reaction comprises providing a reaction mixture comprising the RNA, a primer which will amplify the RNA (e.g., a sequence-specific primer, a random primer, or oligo(dT)s), a reverse transcriptase, and dNTPs, and heating the reaction mixture to a third predetermined temperature for a third predetermined time under conditions to allow the reverse transcriptase to extend the primer.

(3) Sequencing and Genotyping

Another method for determining the presence of a PRKC gene fusion molecule (such as, e.g., IGF2BP3:PRKCA, TANC2:PRKCA, ADCY9:PRKCB, or SPNS1:PRKCB, as disclosed herein) includes: sequencing a portion of the nucleic acid molecule (e.g., sequencing the portion of the nucleic acid molecule that comprises the fusion junction of a PRKC gene fusion), thereby determining that the PRKC gene fusion is present in the nucleic acid molecule. Optionally, the sequence acquired is compared to a reference sequence, or a wild type reference sequence. In one embodiment, the sequence is determined by a next generation sequencing method. In some embodiments, the sequencing is automated and/or high-throughput sequencing. The method can further include acquiring, e.g., directly or indirectly acquiring, a sample, e.g., a tumor or cancer sample, from a patient.

In some embodiments, the sequencing comprises chain terminator sequencing (Sanger sequencing), comprising: providing a reaction mixture comprising a nucleic acid molecule from a biological sample, a primer complementary to a region of the template nucleic acid molecule, a DNA polymerase, a plurality of free nucleotides comprising adenine, thymine, cytosine, and guanine (dNTPs), and at least one chain terminating nucleotide (e.g., at least one di-deoxynucleotide (ddNTPs) chosen from ddATP, ddTTP, ddCTP, and ddGTP), wherein the at least one chain terminating nucleotide is present in a low concentration so that chain termination occurs randomly at any one of the positions containing the corresponding base on the DNA strand; annealing the primer to a single strand of the nucleic acid molecule; extending the primer to allow incorporation of the chain terminating nucleotide by the DNA polymerase to produce a series of DNA fragments that are terminated at positions where that particular nucleotide is used; separating the polynucleotides by electrophoresis (e.g., gel or capillary electrophoresis); and determining the nucleotide order of the template nucleic acid molecule based on the positions of chain termination on the DNA fragments. In some embodiments, the sequencing is carried out with four separate base-specific reactions, wherein the primer or the chain terminating nucleotide in each reaction is labeled with a separate fluorescent label. In other embodiments, the sequencing is carried out in a single reaction, wherein the four chain terminating nucleotides mixed in the single reaction are each labeled with a separate fluorescent label.

In some embodiments, the sequencing comprises pyrosequencing (sequencing by synthesis), comprising: (i) providing a reaction mixture comprising a nucleic acid molecule from a biological sample, a primer complementary to a region of the template nucleic acid molecule, a DNA polymerase, a first enzyme capable of converting pyrophosphate into ATP, and a second enzyme capable using ATP to generates a detectable signal (e.g., a chemiluminescent signal, such as light) in an amount that is proportional to the amount of ATP; (ii) annealing the primer to a single strand of the nucleic acid molecule; (iii) adding one of the four free nucleotides (dNTPs) to allow incorporation of the correct, complementary dNTP onto the template by the DNA polymerase and release of pyrophosphate stoichiometrically; (iv) converting the released pyrophosphate to ATP by the first enzyme; (v) generating a detectable signal by the second enzyme using the ATP; (vi) detecting the generated signal and analyzing the amount of signal generated in a pyrogram; (vii) removing the unincorporated nucleotides; and (viii) repeating steps (iii) to (vii). The method allows sequencing of a single strand of DNA, one base pair at a time, and detecting which base was actually added at each step. The solutions of each type of nucleotides are sequentially added and removed from the reaction. Light is produced only when the nucleotide solution complements the first unpaired base of the template. The order of solutions which produce detectable signals allows the determination of the sequence of the template.

In some embodiments, the method of determining the presence of a PRKC fusion (such as, e.g., IGF2BP3:PRKCA, TANC2:PRKCA, ADCY9:PRKCB, or SPNS1:PRKCB, as disclosed herein) comprises analyzing a nucleic acid sample (e.g., DNA, cDNA, or RNA, or an amplification product thereof) by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of a PRKC fusion (such as, e.g., IGF2BP3:PRKCA, TANC2:PRKCA, ADCY9:PRKCB, or SPNS1:PRKCB, as disclosed herein) comprises analyzing a nucleic acid sample (e.g., DNA, cDNA, or RNA, or an amplification product thereof) by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

II. Methods for Detecting Fusion Proteins

Another aspect of the invention provides a method of detecting the presence of a PRKC fusion protein in a mammal. The method comprises the steps of obtaining a biological sample of a mammal (such as, e.g., a human cancer), and exposing that sample to at least one reagent that detects a PRKC fusion protein (e.g., an antibody that recognizes the PRKC fusion but does not recognize the wild type PRKC or the wild type fusion partner) to determine whether a PRKC fusion protein is present in the biological sample. The detection of a PRKC fusion protein indicates the presence of a mutant PRKC in the mammal (such as, e.g., in the human cancer). In some embodiments, the PRKC fusion protein comprises an amino acid sequence having at least 85%, 90%, 95%, 97%, 98%, or 99% identity with an amino acid sequence of all or part of any one of SEQ ID NOs 2, 4, 6, or 8 or fragments thereof that include the fusion junction. In some embodiments the cancer is lung cancer. In some embodiments, the cancer is lung squamous cell carcinoma. In some embodiments, the cancer is lung adenocarcinoma.

In some embodiments, the reagent that detects a PRKC fusion protein can be detectably labeled with, e.g., a radiolabel, a fluorescent label, a bioluminescent label, a chemiluminescent label, an enzyme label, a binding pair label (e.g., biotin/streptavidin), an antigen label, or can include an affinity tag or identifier (e.g., an adaptor, barcode or other sequence identifier). In some embodiments, the labeled reagent can be detected using, e.g., autoradiography, microscopy (e.g., brightfield, fluorescence, or electron microscopy), ELISA, or immunohistochemistry. In some embodiments, the PRKC fusion protein is detected in a biological sample by a method chosen from one or more of: antibody-based detection (e.g., western blot, ELISA, immunohistochemistry), size-based detection methods (e.g., HPLC or mass spectrometry), or protein sequencing.

(1) Antibody-Based Detection

In some embodiments, the method comprises performing a western blot with polypeptides from a biological sample to detect the presence of a PRKC fusion protein (such as, e.g., IGF2BP3:PRKCA, TANC2:PRKCA, ADCY9:PRKCB, or SPNS1:PRKCB, as disclosed herein). In some embodiments, the western blot comprises the steps of: separating the polypeptides by gel electrophoresis; transferring the polypeptides from the gel to a membrane (e.g., a nitrocellulose or polyvinylidene difluoride (PVDF) membrane); blocking the membrane to prevent nonspecific binding by incubating the membrane in a dilute solution of protein (e.g., 3-5% bovine serum albumin (BSA) or non-fat dry milk in Tris-Buffered Saline (TBS) or I-Block, with a minute percentage (e.g., 0.1%) of detergent, such as, e.g., Tween 20 or Triton X-100); exposing the polypeptides to at least one reagent that detects a PRKC fusion protein (e.g., an antibody that recognizes the PRKC fusion but does not recognize the wild type PRKC or the wild type fusion partner); removing unbound or non-specifically bound reagent by washing; and detecting the binding of the reagent with the target protein. In some embodiments, the method comprises two-step detection: exposing the polypeptides to a primary antibody that specifically binds to a PRKC fusion protein; removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the reagent that detects a PRKC fusion protein (e.g., the fusion specific antibody, or the secondary antibody) is directly labeled for detection. In other embodiments, the reagent is linked to an enzyme, and the method further comprises adding a substrate of the enzyme to the membrane; and developing the membrane by detecting a detectable signal produced by the reaction between the enzyme and the substrate. For example, the reagent may be linked with horseradish peroxidase to cleave a chemiluminescent agent as a substrate, producing luminescence in proportion to the amount of the target protein for detection.

In some embodiments, the method comprises performing ELISA with polypeptides from a biological sample to detect the presence of a PRKC fusion protein (such as, e.g., IGF2BP3:PRKCA, TANC2:PRKCA, ADCY9:PRKCB, or SPNS1:PRKCB, as disclosed herein). In some embodiments, the ELISA is chosen from, e.g., direct ELISA, indirect ELISA, sandwich ELISA, and competitive ELISA.

In one embodiment, the direct ELISA comprises the steps of: attaching polypeptides from a biological sample to a surface; blocking the surface to prevent nonspecific binding by incubating the surface in a dilute solution of protein; exposing the polypeptides to an antibody that specifically binds to a PRKC fusion protein (e.g., an antibody that recognizes the PRKC fusion (such as, e.g., IGF2BP3: PRKCA, TANC2:PRKCA, ADCY9:PRKCB, or SPNS1: PRKCB, as disclosed herein) but does not recognize the wild type PRKC or the wild type fusion partner); removing unbound or non-specifically bound antibody by washing; and detecting the binding of the antibody with the target protein. In some embodiments, the antibody is directly labeled for detection. In other embodiments, the antibody is linked to an enzyme, and the method further comprises adding a substrate of the enzyme; and detecting a detectable signal produced by the reaction between the enzyme and the substrate.

In another embodiment, the indirect ELISA comprises the steps of: attaching polypeptides from a biological sample to a surface; blocking the surface to prevent nonspecific binding by incubating the surface in a dilute solution of protein; exposing the polypeptides to a primary antibody that specifically binds to a PRKC fusion protein (such as, e.g., IGF2BP3:PRKCA, TANC2:PRKCA, ADCY9:PRKCB3, or SPNS1:PRKCB, as disclosed herein); removing unbound or non-specifically bound primary antibody by washing; exposing the polypeptides to a secondary antibody that recognizes the primary antibody; removing unbound or non-specifically bound secondary antibody by washing; and detecting the binding of the secondary antibody. In some embodiments, the secondary antibody is directly labeled for detection. In other embodiments, the secondary antibody is linked to an enzyme, and the method further comprises adding a substrate of the enzyme; and detecting a detectable signal produced by the reaction between the enzyme and the substrate.

In some embodiments, the method comprises performing immunohistochemistry with polypeptides from a biological sample to detect the presence of a PRKC fusion protein (such as, e.g., IGF2BP3:PRKCA, TANC2:PRKCA, ADCY9:PRKCB, or SPNS1:PRKCB, as disclosed herein). In some embodiments, the immunohistochemistry comprises the steps of: fixing a cell or a tissue section (e.g., by paraformaldehyde or formalin treatment); permeabilizing the cell or tissue section to allow target accessibility; blocking the cell or tissue section to prevent nonspecific binding; exposing the cell or tissue section to at least one reagent that detects a PRKC fusion protein (e.g., an antibody that recognizes the PRKC fusion but does not recognize the wild type PRKC or the wild type fusion partner); removing unbound or non-specifically bound reagent by washing; and detecting the binding of the reagent with the target protein. In some embodiments, the reagent is directly labeled for detection. In other embodiments, the reagent is linked to an enzyme, and the method further comprises adding a substrate of the enzyme; and detecting a detectable signal produced by the reaction between the enzyme and the substrate. In some embodiments, the immunohistochemistry may comprise the two-step detection as in the indirect ELISA.

(2) Size-Based Detection Methods

In some embodiments, the method of determining the presence of a PRKC fusion (such as, e.g., IGF2BP3: PRKCA, TANC2:PRKCA, ADCY9:PRKCB, or SPNS1: PRKCB, as disclosed herein) comprises analyzing a protein sample by HPLC. The method may comprise: passing a pressurized liquid solution containing the sample through a column filled with a sorbent, wherein the nucleic acid or protein components in the sample interact differently with the sorbent, causing different flow rates for the different components; separating the components as they flow out the column at different flow rates. In some embodiments, the HPLC is chosen from, e.g., reverse-phase HPLC, size exclusion HPLC, ion-exchange HPLC, and bioaffinity HPLC.

In some embodiments, the method of determining the presence of a PRKC fusion (such as, e.g., IGF2BP3: PRKCA, TANC2:PRKCA, ADCY9:PRKCB, or SPNS1: PRKCB, as disclosed herein) comprises analyzing a protein sample by mass spectrometry. The method may comprise: ionizing the components in the sample (e.g., by chemical or electron ionization); accelerating and subjecting the ionized components to an electric or magnetic field; separating the ionized components based on their mass-to-charge ratios; and detecting the separated components by a detector capable of detecting charged particles (e.g., by an electron multiplier).

Detection of a PRKC gene fusion or a PRKC fusion protein in a patient can lead to assignment of the patient to the newly identified patient population that bears the PRKC fusion. Because this patient population can suffer from or be susceptible to a disorder associated with an aberrant (e.g., constitutive) PRKC activity or expression, or overexpression of PRKC, detection of the PRKC fusion can also lead to diagnosis of such disorder. Thus, a further aspect of the invention provides a method of stratifying a patient population (e.g., assigning a patient, to a group or class) and/or diagnosing a patient, comprising: obtaining a biological sample from the patient, contacting the sample with at least one reagent that detects a PRKC gene fusion or a PRKC fusion protein to determine whether a PRKC fusion is present in the biological sample. The detection of a PRKC fusion indicates that the patient belongs to the newly identified patient population that bears the PRKC fusion, and/or the presence of a disorder associated with aberrant (e.g., constitutive) PRKC activity or expression, or overexpression of PRKC, such as, e.g., a cancer. The detection of a PRKC fusion also identifies a new subtype of cancer, which is characterized by the presence of the PRKC fusion. In some embodiments, the cancer is lung cancer. In some embodiments, the cancer is lung squamous cell carcinoma or lung adenocarcinoma. In certain embodiments, the PRKC fusion is IGF2BP3:PRKCA, TANC2:PRKCA, ADCY9: PRKCB, or SPNS1:PRKCB. In some embodiments, the IGF2BP3:PRKCA fusion has all or part of the nucleotide and/or amino acid sequence (such as, e.g., the fusion junction) set forth in SEQ ID NO:1 and SEQ ID NO:2, respectively. In some embodiments, the TANC2:PRKCA fusion has all or part of the nucleotide and/or amino acid sequence (such as, e.g., the fusion junction) set forth in SEQ ID NO:3 and SEQ ID NO:4, respectively. In some embodiments, the ADCY9:PRKCB fusion has all or part of the nucleotide and/or amino acid sequence (such as, e.g., the fusion junction) set forth in SEQ ID NO:5 and SEQ ID NO:6, respectively. In some embodiments, the SPNS1:PRKCB fusion has all or part of the nucleotide and/or amino acid sequence (such as, e.g., the fusion junction) set forth in SEQ ID NO:7 and SEQ ID NO:8, respectively.

In some embodiments, the PRKC gene fusion or PRKC fusion protein is detected prior to initiating, during, or after, a treatment of a patient with, e.g., a PRKC inhibitor or a PRKC fusion inhibitor. In one embodiment, the PRKC gene fusion or PRKC fusion protein is detected at the time the patient is diagnosed with a cancer. In other embodiment, the PRKC fusion is detected at a pre-determined interval, e.g., a first point in time and at least at a subsequent point in time. In certain embodiments, in response to detection of a PRKC fusion, such as, e.g., IGF2BP3:PRKCA, TANC2:PRKCA, ADCY9:PRKCB, or SPNS1:PRKCB, the method further includes one or more of:

(1) stratifying a patient population (e.g., assigning a patient, to a group or class);

(2) identifying or selecting the patient as likely or unlikely to respond to a treatment, e.g., a PRKC inhibitor treatment (e.g., a kinase inhibitor treatment or an anti-PRKC antibody treatment), or a PRKC fusion inhibitor treatment as described herein;

(3) selecting a treatment regimen, e.g., administering or not administering a preselected therapeutic agent, such as, e.g., a PRKC inhibitor, or a PRKC fusion inhibitor;

(4) prognosticating the time course of the disease in the patient (e.g., evaluating the likelihood of increased or decreased patient survival); or (5) monitoring the effectiveness of treatment (e.g., by detecting a reduction in the level of PRKC gene fusion or fusion protein in a patient sample).

In certain embodiments, upon detection of a PRKC gene fusion or PRKC fusion protein in a patient's biological sample, the patient is identified as likely to respond to a treatment that comprises a PRKC inhibitor, or a PRKC fusion inhibitor. In some embodiments, the PRKC fusion detected is an IGF2BP3:PRKCA fusion. In alternate embodiments, the PRKC fusion detected is a TANC2: PRKCA fusion. In some embodiments, the PRKC fusion detected is an ADCY9:PRKCB fusion. In some embodiments the PRKC fusion detected is an SPNS1:PRKCB fusion.

A further aspect of the invention provides a method of selecting a treatment option by detecting a PRKC fusion. The method comprises obtaining a biological sample from a patient and exposing the sample to at least one reagent that detects a PRKC gene fusion or fusion protein to determine whether a PRKC fusion is present in the biological sample. The detection of the PRKC fusion indicates the likelihood of the patient responding to treatment with a PRKC inhibitor, or a PRKC fusion inhibitor. The method may be augmented or personalized by evaluating the effect of a variety of PRKC, or PRKC fusion inhibitors on the biological sample shown to contain a PRKC fusion to determine the most appropriate inhibitor to administer. In certain embodiments, the PRKC fusion is IGF2BP3:PRKCA, TANC2:PRKCA, ADCY9:PRKCB, or SPNS1:PRKCB. In some embodiments, the IGF2BP3:PRKCA fusion has all or part of the nucleotide and/or amino acid sequence (such as, e.g., the fusion junction) set forth in SEQ ID NO:1 and SEQ ID NO:2, respectively. In some embodiments, the TANC2: PRKCA fusion has all or part of the nucleotide and/or amino acid sequence (such as, e.g., the fusion junction) set forth in SEQ ID NO:3 and SEQ ID NO:4, respectively. In some embodiments, the ADCY9:PRKCB fusion has all or part of the nucleotide and/or amino acid sequence (such as, e.g., the fusion junction) set forth in SEQ ID NO:5 and SEQ ID NO:6, respectively. In some embodiments, the SPNS1: PRKCB fusion has all or part of the nucleotide and/or amino acid sequence (such as, e.g., the fusion junction) set forth in SEQ ID NO:7 and SEQ ID NO:8, respectively.

Methods of Treatment

Alternatively, or in combination with the detection and diagnostic methods described herein, the invention provides method for treating the newly identified patient population and the new PRKC fusion cancer subtype, which are characterized by the presence of a PRKC fusion. The patient population and cancer subtype can be associated with or predict the onset of a condition mediated by aberrant (e.g., constitutive) PRKC activity or expression, or overexpression of PRKC, such as, e.g., a cancer or a tumor harboring a PRKC fusion. The methods comprise administering a therapeutic agent, e.g., a PRKC inhibitor, such as e.g., a kinase inhibitor or an antibody specific to PRKC; or a PRKC fusion inhibitor, i.e., an inhibitor that blocks the activity of the PRKC fusion but not wild type PRKC or wild type fusion partner (such as, e.g., IGF2BP3, TANC2, ADCY9, or SPNS1), such as, e.g., an antibody specific to an IGF2BP3: PRKCA, a TANC2:PRKCA, an ADCY9:PRKCB, or an SPNS1:PRKCB fusion protein, e.g., any one of the antibodies described above; an agent that mimics the pseudosubstrate segment and binds the substrate-binding cavity in the catalytic domain of PRKC, keeping the enzyme inactive; or an RNA inhibitor that recognizes PRKC or the fusion junction of a PRKC gene fusion, including but not limited to siRNA, dsRNA, shRNA, or any other antisense nucleic acid inhibitor, alone or in combination with e.g., other chemotherapeutic agents or procedures, in an amount sufficient to treat a condition mediated by aberrant (e.g., constitutive) PRKC activity or expression, or overexpression of PRKC by one or more of the following: e.g., impeding growth of a cancer, causing a cancer to shrink by weight or volume, extending the expected survival time of the patient, inhibiting tumor growth, reducing tumor mass, reducing size or number of metastatic lesions, inhibiting the development of new metastatic lesions, prolonging survival, prolonging progression-free survival, prolonging time to progression, and/ or enhancing quality of life.

As used herein, and unless otherwise specified, a "therapeutically effective amount" of a compound is an amount sufficient to provide a therapeutic benefit in the treatment or management of a condition mediated by aberrant PRKC expression or activity, or overexpression of PRKC, such as, delaying or minimizing one or more symptoms associated with a cancer or a tumor harboring a PRKC fusion (such as, e.g., IGF2BP3:PRKCA, TANC2:PRKCA. ADCY9: PRKCB, or SPNS1:PRKCB, as described herein). A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the condition mediated by aberrant PRKC expression or activity or overexpression of PRKC, or enhances the therapeutic efficacy of another therapeutic agent.

In certain embodiments, the therapeutic agent is a PRKC inhibitor, or a PRKC fusion inhibitor. In some embodiments, the therapeutic agent is a PRKC inhibitor, e.g., a compound, biological or chemical, which inhibits, directly or indirectly, the expression and/or activity of PRKC. For example, the PRKC inhibitors may be an antibody (such as, e.g., antibodies specific to PRKC, e.g., PRKCA or PRKCB) or a small molecule inhibitor. In some embodiments, the inhibitors may act directly on PRKC itself, modify the activity of PRKC, or inhibit the expression of PRKC. In other embodiments, the inhibitors may indirectly inhibit PRKC activity by inhibiting the activity of proteins or molecules other than PRKC itself. For example, the inhibitors may modulate the activity of regulatory kinases that phosphorylate or dephosphorylate PRKC, interfere with binding of ligands, or inhibit the activity of interacting or downstream proteins or molecules. Exemplary PRKC inhibitors also include kinase inhibitors, which may be a pan-kinase inhibitor with activity against several different kinases or a kinase-specific inhibitor (e.g., a serine/threonine kinase inhibitor, or an inhibitor specific to the kinase activity of PRKC). In some embodiments, the PRKC inhibitor is a PRKC-specific inhibitor.

In other embodiments, the therapeutic agent is a PRKC fusion inhibitor, e.g., a PRKC gene fusion inhibitor or a PRKC protein fusion inhibitor. In some embodiments, the PRKC fusion inhibitor inhibits the expression of nucleic acid encoding a PRKC fusion. Examples of PRKC fusion inhibitors include nucleic acid molecules, for example, antisense molecules, ribozymes, RNAi, or triple helix molecules, that hybridize to a nucleic acid encoding a PRKC fusion (e.g., genomic DNA, or mRNA), or a transcription and/or translation regulatory region, and blocks or reduces mRNA and/or protein expression of a PRKC fusion. In some embodiments, the antisense molecule recognizes the PRKC fusion junction, or an RNA inhibitor, including but not limited to siRNA, dsRNA, and short-hairpin RNA specific to the PRKC fusion junction. In some embodiments, the PRKC fusion is IGF2BP3:PRKCA, TANC2:PRKCA. ADCY9: PRKCB, or SPNS1:PRKCB. Exemplary PRKC fusion inhibitors also include an antibody that recognizes the fusion protein, and/or does not recognize the wild type fusion partners. In some embodiments, the PRKC fusion inhibitors include an antibody that recognizes IGF2BP3:PRKCA, TANC2:PRKCA, ADCY9:PRKCB, or SPNS1:PRKCB fusion protein, and/or does not recognize wild type PRKC, e.g., PRKCA or PRKCB, IGF2BP3, TANC2, ADCY9, or SPNS1. In some embodiments, the PRKC fusion protein (such as, e.g., an IGF2BP3:PRKCA fusion protein, a TANC2:PRKCA fusion protein, an ADCY9:PRKCB fusion protein, or an SPNS1:PRKCB fusion protein) is inhibited by an agent that mimics the pseudosubstrate segment and binds the substrate-binding cavity in the catalytic domain of PRKC, keeping the enzyme inactive.

In some embodiments, the patient to be treated is suffering from lung squamous cell carcinoma or lung adenocarcinoma and the method for treating the condition comprises administering to the patient a therapeutically effective amount of a PRKC inhibitor or a PRKC fusion inhibitor. In some embodiments, the patient to be treated is suffering from lung squamous cell carcinoma, and the method for treating the condition comprises administering to the patient a therapeutically effective amount of a PRKC inhibitor, or a PRKC gene fusion inhibitor or a PRKC fusion protein inhibitor as described above. In some embodiments, the patient to be treated is suffering from lung adenocarcinoma, and the method for treating the condition comprises administering to the patient a therapeutically effective amount of a PRKC inhibitor, or a PRKC gene fusion inhibitor or a PRKC fusion protein inhibitor.

Screening Methods

Therapeutic agents, such as, e.g., PRKC inhibitors, and PRKC fusion inhibitors (gene fusion and fusion protein), used in the therapeutic methods of the invention can be evaluated using the screening assays described herein. Thus, the invention provides a method of identifying an agent useful for treating a condition mediated by aberrant (e.g., constitutive) PRKC activity or expression, or overexpression of PRKC, such as, e.g., a cancer or a tumor harboring a PRKC fusion, such as, e.g., lung squamous cell carcinoma or lung adenocarcinoma, comprising contacting a cell expressing a PRKC gene fusion or PRKC fusion protein with a candidate agent and using one of the detection methods referenced above to determine whether the expression level of the fusion is decreased or a biological function associated with the fusion is altered. In one embodiment, therapeutic agents can be evaluated in a cell-free system, e.g., a cell lysate or in a reconstituted system. In other embodiments, the therapeutic agents are evaluated in a cell in culture, e.g., a cell expressing a PRKC fusion (e.g., a mammalian cell, a tumor cell or cell line, a recombinant cell). In yet other embodiments, the therapeutic agents are evaluated in a cell in vivo (e.g., a PRKC fusion-expressing cell present in a subject, e.g., an animal subject (e.g., an in vivo animal model).

Exemplary parameters to evaluate in determining the efficacy of a therapeutic agent for treating a condition mediated by aberrant (e.g., constitutive) PRKC activity or expression, or overexpression of PRKC, such as, e.g., a cancer or a tumor harboring a PRKC fusion include one or more of:

(i) a change in binding activity, e.g., direct binding of the candidate agent to a PRKC fusion protein or a binding competition between a known ligand and the candidate agent to a PRKC fusion protein:

(ii) a change in kinase activity, e.g., phosphorylation levels of a PRKC fusion protein (e.g., an increased or decreased phosphorylation or autophosphorylation) or a change in phosphorylation of a target of a PRKC kinase—in certain embodiments, a change in kinase activity, e.g., phosphorylation, is detected by any of Western blot (e.g., using an anti-PRKC antibody; or a phosphor-specific antibody, detecting a shift in the molecular weight of a PRKC fusion protein), mass spectrometry, immunoprecipitation, immunohistochemistry, immunomagnetic beads, among others;

(iii) a change in an activity of a cell containing a PRKC fusion (e.g., a tumor cell or a recombinant cell), e.g., a change in proliferation, morphology, or tumorigenicity of the cell;

(iv) a change in tumor present in an animal subject, e.g., size, appearance, or proliferation of the tumor;
(v) a change in the level, e.g., expression level (transcription and/or translation), of a PRKC fusion protein or nucleic acid molecule; or
(vi) a change in an activity of a signaling pathway involving PRKC, e.g., phosphorylation or activity of an interacting or downstream target, or expression level of a target gene.

In some embodiments, the PRKC fusion is an IGF2BP3:PRKCA fusion, a TANC2:PRKCA fusion, an ADCY9:PRKCB fusion, or an SPNS1:PRKCB fusion.

In one embodiment, a change in the activity of a PRKC fusion, or interaction of a PRKC fusion with a downstream ligand detected in a cell free assay in the presence of a candidate agent indicates that the candidate agent will be effective as a therapeutic agent for treatment of a condition mediated by aberrant (e.g., constitutive) PRKC activity or expression, or overexpression of PRKC, such as, e.g., a cancer or a tumor harboring a PRKC fusion.

In other embodiments, a change in an activity of a cell expressing a PRKC fusion, such as, e.g., IGF2BP3:PRKCA, TANC2:PRKCA, ADCY9:PRKCB, or SPNS1:PRKCB, as described herein, (e.g., a mammalian cell, a tumor cell or cell line, a recombinant cell) is detected in a cell in culture. In one embodiment, the cell is a recombinant cell that is modified to express a PRKC fusion nucleic acid, e.g., is a recombinant cell transfected with a PRKC fusion nucleic acid. The transfected cell can show a change in response to the expressed PRKC fusion, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, or transformed morphology, in the presence of the candidate agent can be indicative of an inhibitor of a PRKC fusion. In other embodiments, a change in binding activity or phosphorylation of PRKC or its interacting or downstream proteins or molecules as described herein is detected.

In yet other embodiment, a change in a tumor present in an animal subject (e.g., an in vivo animal model) is detected. In one embodiment, a tumor containing animal or a xenograft comprising cells expressing a PRKC fusion (e.g., tumorigenic cells expressing a PRKC fusion) is employed. The therapeutic agents can be administered to the animal subject and a change in the tumor is evaluated. In one embodiment, the change in the tumor includes one or more of a tumor growth, tumor size, tumor burden, or survival is evaluated. A decrease in one or more of tumor growth, tumor size, tumor burden, or an increased survival is indicative that the candidate agent is an inhibitor or modulator.

In another aspect of the invention provides a method or assay for screening for agents that modulate (e.g., inhibit) the expression or activity of a PRKC fusion as described herein. The method includes contacting e.g., a PRKC fusion, or a cell expressing a PRKC fusion, with a candidate agent; and detecting a change in a parameter associated with a PRKC fusion, e.g., a change in the expression or an activity of the PRKC fusion. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the PRKC fusion is detected, the candidate agent is identified as an inhibitor. In another embodiment, if an increase in expression or activity of the PRKC fusion is detected, the candidate agent is identified as an activator. In certain embodiments, the PRKC fusion is a PRKC gene fusion or PRKC fusion protein, such as, e.g., an IGF2BP3:PRKCA fusion, a TANC2:PRKCA fusion, an ADCY9:PRKCB fusion, or an SPNS1:PRKCB fusion.

In one embodiment, the contacting step is detected in a cell-free system, e.g., a cell lysate or in a reconstituted system. In other embodiments, the contacting step is detected in a cell in culture, e.g., a cell expressing a PRKC fusion (e.g., a mammalian cell, a tumor cell or cell line, a recombinant cell). In yet other embodiments, the contacting step is detected in a cell in vivo (e.g., a PRKC expressing cell present in a subject, e.g., an animal subject (e.g., an in vivo animal model)).

Exemplary parameters evaluated in identifying an agent that modulates the activity of a PRKC fusion, e.g., a PRKC fusion (e.g., an IGF2BP3:PRKCA fusion, a TANC2:PRKCA fusion, an ADCY9:PRKCB fusion, or an SPNS1:PRKCB fusion) include one or more of:
(i) a change in binding activity, e.g., direct binding of the candidate agent to a PRKC fusion protein; a binding competition between a known ligand and the candidate agent to a PRKC fusion protein;
(ii) a change in kinase activity, e.g., phosphorylation levels of a PRKC fusion protein (e.g., an increased or decreased phosphorylation or autophosphorylation) or a change in phosphorylation of a target of a PRKC kinase—in certain embodiments, a change in kinase activity, e.g., phosphorylation, is detected by any of Western blot (e.g., using an anti-PRKC antibody; or a phosphor-specific antibody, detecting a shift in the molecular weight of a PRKC fusion protein), mass spectrometry, immunoprecipitation, immunohistochemistry, immunomagnetic beads, among others;
(iii) a change in an activity of a cell containing a PRKC fusion (e.g., a tumor cell or a recombinant cell), e.g., a change in proliferation, morphology or tumorigenicity of the cell;
(iv) a change in tumor present in an animal subject, e.g., size, appearance, proliferation, of the tumor;
(v) a change in the level, e.g., expression level (transcription and/or translation), of a PRKC fusion protein or nucleic acid molecule; or
(vi) a change in an activity of a signaling pathway involving PRKC, e.g., phosphorylation or activity of an interacting or downstream target, or expression level of a target gene.

Methods for Validating PRKC Fusions

PRKC gene fusions, such as, e.g., PRKC gene fusions (e.g., IGF2BP3:PRKCA gene fusion, TANC2:PRKCA gene fusion, ADCY9:PRKCB gene fusion, or SPNS1:PRKCB gene fusion) may be evaluated to ensure that the breakpoints are in-frame and can produce a protein product containing the full kinase domain, i.e., that the breakpoint occurs such that complete triplet codons are intact, and that the RNA sequence will produce a viable protein. The PRKC gene fusion can be transfected into cells to confirm that the protein is functionally active with respect to kinase activity and oncogenic activity. cDNA encoding the PRKC fusion protein can be produced by standard solid-phase DNA synthesis. Alternatively the PRKC fusion cDNA can be produced by RT-PCR using tumor mRNA extracted from samples containing the gene fusion. The DNA amplified can be subcloned into an appropriate vector and characterized by DNA sequence analysis or in vitro/in vivo expression analyses.

Expression vectors containing the PRKC gene fusion (such as, e.g., a PRKC gene fusion, e.g., an IGF2BP3:PRKCA gene fusion, a TANC2:PRKCA gene fusion, an ADCY9:PRKCB gene fusion, or an SPNS1:PRKCB gene fusion) can be introduced into host cells to thereby produce a PRKC fusion protein (such as, e.g., a PRKC fusion protein, e.g., an IGF2BP3:PRKCA fusion protein, a TANC2:PRKCA fusion protein, an ADCY9:PRKCB fusion protein, or an SPNS1:PRKCB fusion protein). The PRKC fusion protein expression vector can be a yeast expression vector, a vector for expression in insect cells, e.g., a baculovirus expression vector, or a vector suitable for expression in mammalian cells. Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell.

Cells harboring the expression vector carrying the recombinant PRKC gene fusion can then be tested for production of the unique fusion protein via standard Western blotting using either an antibody probe that detects the gene product itself or that recognizes a tag peptide (e.g., FLAG tag) that can be added to the gene product via the expression vector (using standard, commercially available reagents). Western blotting can be used to confirm the ectopic expression of the encoded PRKC fusion protein by comparing the samples from cells transfected with the vector containing the PRKC gene fusion cDNA to cells transfected with the empty expression vector. The functional activity can be assessed by measuring the level of phosphorylation on the kinase or substrate. Comparison of the level of phosphorylation activity between the wild type (normal) form of PRKC and the PRKC fusion protein can indicate if the PRKC fusion protein has elevated activity that could drive oncogenic activity. Whether the PRKC gene fusion is oncogenic can be assessed by measuring capacity of the expressed PRKC fusion protein to transform cells, that is, to enable cells to grow and proliferate under conditions which are not permissive for growth of normal cells. One commonly used method of measuring the transforming activity of a kinase is by assessing if expression of the gene product can allow BaF3 cells to grow in the absence of the growth factor IL3, which is required for the survival and growth of BaF3 cells. Another assay for measuring transforming activity is a soft agar growth assay. This is another standard method which tests the capacity of an introduced gene product to confer the ability to grow in a soft agar matrix, or anchorage-independent conditions. These methods and others can be used to test the oncogenic activity of a PRKC gene fusion (such as, e.g., an IGF2BP3:PRKCA gene fusion, a TANC2:PRKCA gene fusion, an ADCY9:PRKCB gene fusion, or an SPNS1:PRKCB gene fusion) and provide a level of validation of a PRKC fusion protein (such as, e.g., an IGF2BP3:PRKCA fusion protein, a TANC2:PRKCA fusion protein, an ADCY9:PRKCB fusion protein, or an SPNS1:PRKCB fusion protein) as a potential target for treating patients that harbor these fusions.

A change in an activity of a cell can be detected in a cell in culture, e.g., a cell expressing a fusion (e.g., a mammalian cell, a tumor cell or cell line, a recombinant cell). The transfected cell can show a change in response to the expressed fusion, e.g., increased proliferation, changes in morphology, increased tumorigenicity, and/or an acquired transformed phenotype.

To further validate the biological implication of the gene fusion, a change in any of the activities of the cell, e.g., the recombinant cell, in the presence of a known inhibitor of one of the fusion partners, e.g., a PRKC inhibitor, can be detected. For example, a decrease in one or more of: proliferation, tumorigenicity, and transformed morphology, in the presence of the PRKC inhibitor can be indicative of an inhibitor of a fusion. In other embodiments, a change in binding activity or phosphorylation of PRKC or its interacting or downstream proteins or molecules is detected.

All publications and patents mentioned herein are hereby incorporated by reference in their entirety as if each individual publication or patent was specifically and individually indicated to be incorporated by reference. To the extent publications and patents or patent applications incorporated by reference contradict the disclosure contained in the specification, the specification will supersede any contradictory material. Unless otherwise required by context, singular terms shall include the plural and plural terms shall include the singular. The use of "or" means "and/or" unless stated otherwise. The use of the term "including," as well as other forms, such as "includes" and "included," is not limiting. All ranges given in the application encompass the endpoints unless stated otherwise.

Those skilled in the art will recognize, or be able to ascertain using no more than routine experimentation, many equivalents to the specific embodiments of the invention described herein. Such equivalents are intended to be encompassed by the following claims.

We claim:

1. A method of detecting in a patient a TANC2:PRKCA fusion, said method comprising:

a) contacting a biological sample from the patient with an oligonucleotide that hybridizes to or amplifies the TANC2:PRKCA fusion of SEQ ID NO:3 or a portion thereof comprising a fusion junction; and b) detecting (i) binding between the TANC2:PRKCA fusion and the oligonucleotide or (ii) detecting amplification of the TANC2:PRKCA fusion.

2. The method of claim 1, wherein the oligonucleotide hybridizes under stringent conditions to:

a) a fragment of SEQ ID NO:3 comprising nucleotides 134-146 of SEQ ID NO:3; or b) a complementary oligonucleotide of a).

3. The method of claim 1, wherein the patient is suffering from or susceptible to a cancer.

4. The method of claim 3, wherein the cancer is lung cancer.

5. The method of claim 3, wherein the cancer is lung squamous cell carcinoma or lung adenocarcinoma.

6. The method of claim 5, wherein the cancer is lung squamous cell carcinoma.

7. The method of claim 5, wherein the cancer is lung adenocarcinoma.

* * * * *